(12) United States Patent
Letai et al.

(10) Patent No.: US 10,393,733 B2
(45) Date of Patent: Aug. 27, 2019

(54) DYNAMIC BH3 PROFILING

(71) Applicant: Dana-Farber Cancer Institute, Inc., Boston, MA (US)

(72) Inventors: Anthony Letai, Medfield, MA (US); Juan Jose Montero Boronat, Brookline, MA (US); Jeremy Ryan, Somerville, MA (US)

(73) Assignee: Dana-Farber Cancer Institute, Inc., Boston, MA (US)

( * ) Notice: Subject to any disclaimer, the term of this patent is extended or adjusted under 35 U.S.C. 154(b) by 251 days.

(21) Appl. No.: 14/429,272

(22) PCT Filed: Sep. 19, 2013

(86) PCT No.: PCT/US2013/060707
§ 371 (c)(1),
(2) Date: Mar. 18, 2015

(87) PCT Pub. No.: WO2014/047342
PCT Pub. Date: Mar. 27, 2014

(65) Prior Publication Data
US 2015/0362479 A1 Dec. 17, 2015

Related U.S. Application Data

(60) Provisional application No. 61/702,967, filed on Sep. 19, 2012.

(51) Int. Cl.
*G01N 33/50* (2006.01)

(52) U.S. Cl.
CPC ..... *G01N 33/5023* (2013.01); *G01N 33/5008* (2013.01); *G01N 33/5011* (2013.01); *G01N 33/5014* (2013.01); *G01N 33/5032* (2013.01); *G01N 33/5079* (2013.01); *G01N 33/5094* (2013.01); *G01N 2800/52* (2013.01)

(58) Field of Classification Search
CPC ........... G01N 33/5023; G01N 33/5011; G01N 33/5008; G01N 33/5014; G01N 33/5032; G01N 33/5079; G01N 33/5094; G01N 2800/52
See application file for complete search history.

(56) References Cited

U.S. PATENT DOCUMENTS

| 4,522,811 A | 6/1985 | Eppstein et al. |
| 4,676,980 A | 6/1987 | Segal et al. |

(Continued)

FOREIGN PATENT DOCUMENTS

| JP | 2009-532033 A | 9/2009 |
| WO | WO 91/00360 A1 | 1/1991 |

(Continued)

OTHER PUBLICATIONS

Ryan et al. Heightened mitochondrial priming is the basis for apoptotic hypersensitivity of CD4+ CD8+ thymocytes. PNAS 107 (29): 12895-12900 (Jul. 20, 2010).*

(Continued)

*Primary Examiner* — Gailene Gabel
(74) *Attorney, Agent, or Firm* — Wolf, Greenfield & Sacks, P.C.

(57) ABSTRACT

The present invention provides methods of predicting cell sensitivity or resistance to a therapeutic agent.

14 Claims, 18 Drawing Sheets
Specification includes a Sequence Listing.

(56) References Cited

U.S. PATENT DOCUMENTS

| | | | |
|---|---|---|---|
| 4,816,567 A | 3/1989 | Cabilly et al. | |
| 4,946,778 A | 8/1990 | Ladner et al. | |
| 5,225,539 A | 7/1993 | Winter | |
| 5,545,806 A | 8/1996 | Lonberg et al. | |
| 5,545,807 A | 8/1996 | Surani et al. | |
| 5,569,825 A | 10/1996 | Lonberg et al. | |
| 5,625,126 A | 4/1997 | Lonberg et al. | |
| 5,633,425 A | 5/1997 | Lonberg et al. | |
| 5,661,016 A | 8/1997 | Lonberg et al. | |
| 5,674,980 A | 10/1997 | Frankel et al. | |
| 5,804,604 A | 9/1998 | Frankel et al. | |
| 5,916,771 A | 6/1999 | Hori et al. | |
| 5,939,598 A | 8/1999 | Kucherlapati et al. | |
| 5,965,703 A | 10/1999 | Horne et al. | |
| 7,064,193 B1 | 6/2006 | Cory et al. | |
| 7,714,005 B2* | 5/2010 | Chen | C07D 277/34 514/369 |
| 7,868,133 B2 | 1/2011 | Korsmeyer et al. | |
| 8,221,966 B2 | 7/2012 | Letai | |
| 9,360,473 B2 | 6/2016 | Cardone | |
| 15,022,987 * | 6/2016 | Letai et al. | G01N 33/5011 |
| 9,540,674 B2* | 1/2017 | Letai | G01N 33/5011 |
| 9,856,303 B2 | 1/2018 | Korsmeyer et al. | |
| 9,902,759 B2 | 2/2018 | Korsmeyer et al. | |
| 2002/0115613 A1 | 8/2002 | Kumar | |
| 2004/0171809 A1 | 9/2004 | Korsmeyer et al. | |
| 2007/0027175 A1 | 2/2007 | Shaughnessy et al. | |
| 2008/0199890 A1 | 8/2008 | Letai | |
| 2008/0234201 A1 | 9/2008 | Korsmeyer et al. | |
| 2010/0286057 A1 | 11/2010 | Walensky et al. | |
| 2011/0130309 A1* | 6/2011 | Cardone | A61K 49/0004 506/18 |
| 2011/0154522 A1 | 6/2011 | Korsmeyer et al. | |
| 2013/0122492 A1 | 5/2013 | Khosravi et al. | |
| 2013/0149718 A1 | 6/2013 | Letai | |
| 2016/0200786 A1 | 7/2016 | Korsmeyer et al. | |
| 2016/0231314 A1 | 8/2016 | Ryan et al. | |
| 2016/0258933 A1 | 9/2016 | Letai | |
| 2017/0184567 A1 | 6/2017 | Letai | |
| 2018/0120297 A1* | 5/2018 | Letai | G01N 33/5014 |
| 2018/0128813 A1* | 5/2018 | Letai | G01N 33/5014 |
| 2018/0244740 A1 | 8/2018 | Korsmeyer et al. | |

FOREIGN PATENT DOCUMENTS

| | | |
|---|---|---|
| WO | WO 92/20373 A1 | 11/1992 |
| WO | WO 93/08829 A1 | 5/1993 |
| WO | WO 94/02602 A1 | 2/1994 |
| WO | WO 94/11026 A2 | 5/1994 |
| WO | WO 96/27011 A1 | 9/1996 |
| WO | WO 96/33735 A1 | 10/1996 |
| WO | WO 96/34096 A1 | 10/1996 |
| WO | WO 97/05265 A1 | 2/1997 |
| WO | WO 99/53049 A1 | 10/1999 |
| WO | WO 00/59526 A1 | 10/2000 |
| WO | WO 01/12661 A2 | 2/2001 |
| WO | WO 02/20568 A2 | 3/2002 |
| WO | WO 03/040168 A2 | 5/2003 |
| WO | WO 2004/022580 A2 | 3/2004 |
| WO | WO 2004/058804 A1 | 7/2004 |
| WO | WO 2005/044839 A2 | 5/2005 |
| WO | WO 2006/099667 A1 | 9/2006 |
| WO | WO 2007/123791 A2 | 11/2007 |
| WO | 2008/021484 A2 | 2/2008 |
| WO | WO 2010/147961 A1 | 12/2010 |
| WO | 2013/170176 A2 | 11/2013 |
| WO | WO 2013/188978 A1 | 12/2013 |
| WO | WO 2014/047342 A1 | 3/2014 |
| WO | 2015/010094 A1 | 1/2015 |
| WO | 2015/042249 A1 | 3/2015 |
| WO | 2016/176288 A1 | 11/2016 |
| WO | 2016/176299 A1 | 11/2016 |

OTHER PUBLICATIONS

Polster et al. BH3 Death Domain Peptide Induces Cell-Type Selective Mitochondrial Outer Membrane Permeability. The Journal of Biological Chemistry 276 (41): 37887-37894 (Oct. 2001).*
Chonghalie et al. Pretreatment Mitochondrial Priming Correlates with Clinical Response to Cytotoxic Chemotherapy. Science 334 (6059): 1129-1133 (Nov. 25, 2011).*
Davids et al. Targeting the B-Cell Lymphoma/Leukemia 2 Family in Cancer. Journal of Clinical Oncology 30 (25): 3127-3135 (Sep. 1, 2012).*
Letai. The BCL-2 network: Mechanistic insights and therapeutic potential. Drug Discovery Today: Disease Mechanisms 2 (2): 145-151 (2005).*
Campos et al. (Method for Monitoring of Mitochondrial Cytochrome c Release During Cell Death: Immunodetection of Cytochrome c by Flow Cytometry After Selective Permeabilization of the Plasma Membrane. Cytometry Part A 69A 515-523 (2006).*
Supplementary Partial European Search Report for EP03749602.3 dated Jun. 7, 2006.
Supplementary Partial European Search Report for EP03749602.3 dated Sep. 28, 2006.
International Search Report for PCT/US2003/028482 dated Dec. 8, 2005.
International Search Report and Written Opinion for PCT/US2007/008055 dated Jan. 2, 2008.
International Preliminary Report on Patentability for PCT/U2007/008055 dated Sep. 30, 2008.
International Search Report and Written Opinion for PCT/US2013/060707 dated Jan. 9, 2014.
International Preliminary Report on Patentability for PCT/US2013/060707 dated Apr. 2, 2015.
International Search Report and Written Opinion for PCT/US2014/056284 dated Dec. 31, 2014.
Adams, et al., The Bcl-2 Protein Family: Arbiters of Cell Survival. Science. 1998;281(5381):1322-1326.
Ait-Ikhlef et al. The motoneuron degeneration in the wobbler mouse is independent of the overexpression of a Bcl2 transgene in neurons. Neurosci. Lett. 1995;199:163-6.
Bae et al., Underphosphorylated BAD interacts with diverse antiapoptotic Bcl-2 family proteins to regulate apoptosis. Apoptosis. 2001;6:319-30.
Bouillet et al., Proapoptotic Bcl-2 Relative Bim Required for Certain Apoptotic Responses, Leukocyte Homeostatis, and to Preclude Autoimmunity. Science. 1999;286:1735-8.
Boyd et al., Bik, a novel death-inducing protein shares a distinct sequence motif with Bcl-2 family proteins and interacts with viral and cellular survival-promoting proteins. Oncogene. 1995;11:1921-8.
Brady et al., Reflections on a peptide. Nature. 1994;368:692-3.
Brennan et al., Preparation of Bispecific Antibodies by Chemical Recombination of Monoclonal Immunoglobulin $G_1$ Fragments. Science. 1985;229:81.
Calin et al., A MicroRNA Signature Associated with Prognosis and Progression in Chronic Lymphocytic Leukemia. N. Engl. J. Med. 2005;353:1793-801.
Caron et al., Engineered Humanized Dimeric Forms of IgG Are More Effective Antibiotics. J. Exp. Med. 1992;176:1191-5.
Cartron et al., The first α Helix of Bax Play a Necessary Role in Its Ligand-Induced Activation by the BH3-Only Proteins Bid and PUMA. Mol. Cell 2004;16:807-18.
Certo et al., Mitochondria Primed by Death Signals Determine Cellular Addiction to Antiapoptotic BCL-2 Family Members. Cancer Cell. May 2006;9:351-65.
Chen et al., Caspase cleavage of $Bim_{EL}$ triggers a positive feedback amplification of apoptotic signaling. Proc. Natl. Acad. Sci. USA. 2004;101(5):1235-40.
Chen et al., Differential Targeting of Prosurvival Bcl-2 Proteins by Their BH3-Only Ligands Allows Complementary Apoptotic Function. Mol. Cell. 2005;17:393-403.
Cheng et al., Bax-independent inhibition of apoptosis by $Bcl-X_L$. Nature. 1996;379:554-6.

(56) References Cited

OTHER PUBLICATIONS

Cheng et al., BCL-2, BCL-$X_L$ Sequester BH3 Domain-Only Molecules Preventing BAX- and BAK-Mediated Mitochondrial Apoptosis. Mol. Cell. 2001;8:705-11.
Chipuk et al., Direct Activation of Bax by p53 Mediates Mitochondrial Membrane Permeabilization and Apoptosis. Science. 2004;303:1010-4.
Chittenden et al., A conserved domain in Bak, distinct form BH1 and BH2, mediates cell death and protein binding functions. EMBO J. 1995;14(22):5589-96.
Chittenden et al., Induction of apoptosis by the Bcl-2 homologue Bak. Nature. 1995;374(6524):733-6.
Chonghaile et al., Pretreatment mitochondrial priming correlates with clinical response to cytotoxic chemotherapy. Science. Nov. 25, 2011;334(6059):1129-33. doi: 10.1126/science.1206727. Epub Oct. 27, 2011.
Cole et al., The EBV-Hybridoma technique and its application to human lung cancer. Monoclonal Antibodies and Cancer Therapy. 1985;77-96.
Cory et al., The Bcl2 Family: Regulators of the Cellular Life-Or-Death Switch. Nat. Rev. Cancer. 2002;2(9):647-56.
Cosulich et al., Regulation of apoptosis by BH3 domains in a cell-free system. Curr. Biol. 1997;7(12):913-20.
Cote et al., Generation of human monoclonal antibiotics reactive with cellular antigens. Proc. Natl. Acad. Sci. USA. 1983;80:2026-30.
Czabotar et al., Bax Activation by Bim? Cell Death and Differentiation. Sep. 2009;16:1187-91.
Davids et al., BH3 profiling demonstrates that restoration of apoptotic priming contributes to increased sensitivity to PI3K inhibition in stroma-exposed chronic lymphocytic leukemia cells. Blood 118(21). Nov. 18, 2011. Abstract.
Davids et al., Targeting the B-cell lymphoma/leukemia 2 family in cancer. J Clin Oncol. Sep. 1, 2012;30(25):3127-35. doi: 10.1200/JCO.2011.37.0981. Epub May 29, 2012.
Degrado, Designs of peptides and proteins. Adv Protein Chem. 1988;39:51-124.
Deng et al., BH3 Profiling Identifies Three Distinct Classes of Apoptotic Blocks to Predict Response to ABT-737 and Conventional Chemotherapeutic Agents. Cancer Cell. Aug. 2007;12:171-85.
Derenne et al., Antisense strategy shows that Mcl-1 rather than Bcl-2 or Bcl-xL is an essential survival protein of human myeloma cells. Blood. 2002;100:194-9.
Desagher et al., Bid-induced Conformational Change of Bax Is Responsible for Mitochondrial Cytochrome c Release during Apoptosis. J. Cell Biol. 1999;144(5):891-901.
Di Lisa et al., Mitochondrial Function and Cell Injury in Single Cardiac Myocytes Exposed to Anoxia and Reoxygenation. Transplant Proc. 1995;27(5):2829-30.
Di Lisa et al., Mitochondrial membrane potential in single living adult rat cardiac myocytes exposed to anoxia or metabolic inhibition. J. Physiol. 1995;486(1):1-13.
Dohner et al., Genomic Aberrations and Survival in Chronic Lymphocytic Leukemia. N. Engl. J. Med. 2000;343:1910-16.
Egle et al., Bim is a suppressor of Myc-induced mouse B cell leukemia. Proc. Natl. Acad. Sci. USA. 2004;101(16):6164-9.
Ellerby, et al., Anti-cancer activity of targeted pro-apoptotic peptides. Nat. Med. 1999;5(9):1032-8.
Elliott et al., Intercellular Trafficking and Protein Delivery by a Herpesvirus Structural Protein. Cell. 1997;88:223-33.
Eskes et al., Bid Induces the Oligomerization and Insertion of Bax into the Outer Mitochondrial Membrane. Mol. Cell. Biol. 2000;20(3):929-35.
Fanidi et al., Cooperative interaction between c-myc and -2 proto-oncogenes. Nature. 1992;359:554-6.
Fishwild et al., High-avidity human IgGk monoclonal antibodies from a novel strain of minilocus transgenic mice. Nature Biotechnology. 1996;14:845-51.
Frankel et al., Activity of synthetic peptides from the Tat protein of human immunodeficiency virus type 1. Proc. Natl. Acad. Sci. USA. 1989;86:7397-401.
Fuchs et al., Pathway for Polyarginine Entry into Mammalian Cells. Biochemistry Mar. 2004;43(9):2438-44.
Futaki et al., Arginine-rich Peptides: An Abundant Source of Membrane-Permeable Peptides Having Potential as Carriers for Intracellular Protein Delivery. J. Biol. Chem. 2001;276(8):5836-40.
Green et al., A matter of life and death. Cancer Cell. 2002;1:19-30.
Green et al., The Pathophysiology of Mitochondrial Cell Death. Science. 2004;305:626-9.
Green, Life, Death, BH3 Profiles, and the Salmon Mousse. Cancer Cell. Aug. 2007;12:97-9.
Griffiths et al., Cell Damage-induced Conformational Changes of the Pro-Apoptotic Protein Bak In Vivo Precede the Onset of Apoptosis. J. Cell Biol. 1999;144(5):903-14.
Gross et al., Enforced dimerization of BAX results in its translocation, mitochondrial dysfunction and apoptosis. EMBO J. 1998;17(14):3878-85.
Grosschedl et al., Introduction of a μ immunoglobulin gene into the mouse germ line: specific expression in lymphoid cells and synthesis of functional antibody. Cell. 1984;38:647-58.
Gruber et al., Efficient Tumor Cell Lysis Mediated by a Bispecific Single Chain Antibody Expressed in *Escherichia coli*. J. Immunol. 1994;152:5368-74.
Gul et al., Apoptotic blocks and chemotherapy resistance: strategies to identify Bcl-2 protein signatures. Briefings in Functional Genomics and Proteomics. Jan. 2008;7(1):27-34.
Hanahan et al., Heritable formation of pancreatic β-cell tumors in transgenic mice expressing recombinant insulin/simian virus 40 oncogenes. Nature. 1985;315:115-22.
Hanahan et al., The Hallmarks of Cancer. Cell. 2000;100:57-70.
Hans et al., Beta-carbolines induce apoptosis in cultured cerebellar granule neurons via the mitochondrial pathway. Neuropharmacology. Jan. 2005;48(1):105-17.
Harada et al., Survival factor-induced extracellular signal-regulated kinase phosphorylates BIM, inhibiting its association with BAX and proapoptotic activity. Proc. Natl. Acad. Sci. USA. 2004;101(43):15313-7.
Hemann et al., Evasion of the p53 tumour surveillance network by tumour-derived MYC mutants. Nature. 2005;436:807-11.
Hemann et al., Suppression of tumorigenesis by the p53 target PUMA. Proc. Natl. Acad. Sci. USA. 2004;101(25):9333-8.
Hengartner et al., C. elegans Cell Survival Gene ced-9 Encodes a functional Homolog of the Mammalian Proto-Oncogene bcl-2. Cell. 1994;76:665-76.
Holinger et al., Bak BH3 Peptides Antagonize Bcl-x.sub.L Function and Induce Apoptosis through Cytochrome c-independent Activation of Caspases. J. Biol. Chem. 1999;274(19):13298-304.
Holliger et al., Diabodies: Small bivalent and bispecific antibody fragments. Proc. Natl. Acad. Sci. USA. 1993;90:6444-8.
Hoogenboom et al., By-passing Immunisation, Human Antibodies from Synthetic Repertoires of Germline VH Gene segments rearranged in Vitro. J. Mol. Biol. 1992;227:381-8.
Hopp et al., Prediction of protein antigenic determinants from amino acid sequences. Proc. Natl. Acad. Sci. USA. 1981;78:3824-8.
Hsu et al., Nonionic Detergents Induce Dimerization among Members of the Bcl-2 Family. J. Biol. Chem. 1997;272(21):13829-34.
Huang et al., BH3-Only Proteins—Essential Initiators of Apoptotic Cell Death. Cell. 2000;103:839-42.
Huse et al., Generation of a large Combinatorial Library of the Immunoglobulin Repertoire in Phage Lambda. Science. 1989;246:1275-81.
Inohara et al., Harakiri, a novel regulator of cell death, encodes a protein that activates apoptosis and interacts selectively with survival-promoting proteins Bcl-2 and Bcl-$X_L$. Embo J. 1997;16(7):1686-94.
Jackson et al., Heat shock induces the release of fibroblast growth factor 1 from NIH 3T3 cells. Proc. Natl. Acad. Sci. USA. 1992;89:10691-5.
Jameson et al., A rationally designed CD4 analogue inhibits experimental allergic encephalomyelitis. Nature. 1994; 368:744-6.

(56) References Cited

OTHER PUBLICATIONS

Jones et al., Nature, Replacing the complementarily-determining regions in a human antibody with those from a mouse. 1986;321:522-5.
Jonkers et al., Oncogene addiction: Sometimes a temporary slavery. Cancer Cell. 2004;6:535-8.
Kelekar et al., Bad is a BH3 Domain-Containing Protein that Forms an Inactivating Dimer with Bcl-$X_L$. Mol. Cell Biol. 1997;17(12):7040-6.
Kelekar et al., Bcl-2-family proteins: the role of the BH3 domain in apoptosis. Trends Cell Biol. 1998;8:324-30.
Kohler et al., Continuous cultures of fused cells secreting anti-body of predefined specificity. Nature. 1975;256:495-7.
Kostelny et al., Formation of a Bispecific antibody by the Leucine Zippers. J. Immunol. 1992;148(5):1547-53.
Kozbor et al., The production of monoclonal antibodies from human lymphocytes. Immunol Today. 1983;4:72-9.
Kozbor, A human hybrid Myeloma for production of human monoclonal antibodies. J. Immunol. 1984;133:3001-5.
Krieg, Mechanisms and applications of immune stimulatory CpG oligodeoxynucleotides. Biochim Biophys Acta. 1999;1489(1):107-16.
Kuwana et al., BH3 Domains of BH3-Only Proteins Differentially Regulate Bax-Mediated Mitochondrial Membrane Permeabilization Both Directly and Indirectly. Mol. Cell. 2005;17:525-35.
Kuwana et al., Bid, Bax, and Lipids Cooperate to Form Supramolecular Openings in the Outer Mitochondrial Membrane. Cell. 2002;111:331-42.
Kyte et al., A Simple Method for displaying the Hydropathic Character of a protein. J. Mol. Biol. 1982;157:105-42.
La Vieira, et al., Cell permeable BH3-peptides overcome the cytoprotective effect of Bcl-2 and Bcl-$X_L$. Oncogene. 2002;21(13):1963-77.
Leo et al., Characterization of the Antiapoptotic Bcl-2 Family Member Myeloid Cell Leukemia-1 (Mc1-1) and the Stimulation of Its Message by Gonadotropins in the Rat Ovary. Endocrinol. 1999;140(12):5469-77.
Letai et al., Antiapoptotic BcL-2 is required for maintenance of a model leukemia. Cancer Cell. 2004;6:241-9.
Letai et al., Distinct BH3 domains either sensitize or activate mitochondrial apoptosis, serving as prototype cancer therapeutics. Cancer Cell. Sep. 2002;2(3):183-92.
Letai, The BCL-2 network: Mechanistic insights and therapeutic potential. Drug Disc.Today: Disease Mechanisms. 2005;2(2):145-51.
Letai, BH3 domains as BCL-2 inhibitors: prototype cancer therapeutics. Expert Opin Biol Ther. Apr. 2003;3(2):293-304.
Li et al., tsg 101: A novel tumor susceptibility gene isolated by controlled Homozygous functional knockout of Allelic Loci in Mammalian Cells. Cell. 1996;85:319-29.
Li et al., Cleavage of BID by Caspase 8 Mediates the Mitochondrial Damage in the Fas Pathway of Apoptosis. Cell. 1998;94(4):491-501.
Li et al., Endonuclease G is an apoptotic DNase when released from mitochondria. Nature. 2001;412:95-9.
Liu et al., Bax conformational change is a crucial step for PUMA-mediated apoptosis in human leukemia. Biochem Biophys Res Commun. 2003;310(3):956-62.
Lonberg et al., Antigen-specific human antibodies from mice comprising four distinct genetic modifications. Nature. 1994;368:856-9.
Lonberg et al., Human Antibodies from Transgenic Mice. Intern Rev Immunol. 1995;13:65-93.
Luo et al., Bid, a Bc12 interacting protein, mediates cytochrome c release from mitochondria in response to activation of cell surface death receptors, Cell. 1998;94(4):481-90.
Lutter et al., The pro-apoptotic Bcl-2 family member tBid localizes to mitochondrial contact sites. BMC Cell Biology. 2001;2:22.
Marani et al., Identification of Novel Isoforms of the BH3 Domain Protein Bim which Directly Activate Bax to Trigger Apoptosis. Mol Cell Biol. 2002;22(11):3577-89.

Marks et al., By-passing Immunization human Antibodies from v-gene libraries displayed on phage. J. Mol. Biol. 1991;222:581.
Marks et al., By-passing immunization: building high affinity human antibodies by chin shuffling. Bio/Technology. 1992;10:779-83.
Martin, Opening the Cellular Poison Cabinet. Science. Dec. 2010;330:1330-1.
Mason et al., The Hypogonadal mouse: reproductive functions restored by gene therapy. Science. 1986;234:1372-8.
Matsushita et al., A high-efficiency protein transduction system demonstrating the role of PKA in long-lasting long-term potentiation. J. Neuroscience. 2001;21(16):6000-7.
Matsuzaki, Why and how are peptide-lipid interactions utilized for self-defense? Biochem. Soc. Transactions. 2001;29:598-601.
McDonnell et al., bcl-2-Immunoglobulin Transgenic Mice Demonstrate Extended B Cell Survival and Follicular Lymphoproliferation. Cell. 1989;57:79-88.
Means et al., Modifications to change properties in Chemical Modification of Protein. 1974. Chapter 3, pp. 35-54, Holden-Day.
Milstein et al., Hybrid hybridomas and their use in immunohistochemistry. Nature. 1983;305:537-9.
Montero et al., Drug-induced death signaling strategy rapidly predicts cancer response to chemotherapy. Cell. Feb. 26, 2015;160(5):977-90. doi:10.1016/j.cell.2015.01.042.
Morrison et al., Success in specification. Nature. 1994;368:812-3.
Muchmore et al., X-ray and NMR structure of human Bcl-x.sub.L, an inhibitor of programmed cell death. Nature. 1996;381:335-41.
Munson et al., Ligand: A Versatile Computerized Approach for Characterization of Ligand-Binding Systems. Analytical Biochemistry. 1980;107:220-39.
Nakano et al., PUMA, a Novel Proapoptotic Gene, is Induced by p53. Mol. Cell. 2001;7:683-94.
Narita, et al., bax interacts with the permeability transition pore to induce permeability transition and cytochrome c release in isolated mitochondria. Proc. Natl. Acad. Sci. USA. 1998;95:14681-6.
Neuberger et al., Generating high-avidity human Mabs in mice. Nature Biotechnology. 1996;14:826.
O'Brien et al., Phase I and II Multicenter Study of Oblimersen Sodium, a Bcl-2 Antisense Oligonucleotide, in Patients With Advanced Chronic Lymphocytic Leukemia. J. Clin. Oncol. 2005;23(30):7697-702.
O'Connor et al., Bim: a novel member of the Bcl-2 family that promotes apoptosis. Embo J. 1998;17(2):384-95.
Oda et al., Noxa, a BH3-Only Member of the Bcl-2 Family and Candidate Mediator of p53-Induced Apoptosis. Science. 2000;288:1053-8.
Oh et al., Conformational Changes in BID, a Pro-apoptotic BCL-2 Family Member, upon Membrane Binding. J. Biol. Chem. 2005;280(1):753-67.
Oltersdorf et al., An inhibitor of Bcl-2 family proteins induces regression of solid tumours. Nature. 2005;435:677-81.
Opferman et al., Development and maintenance of B and T lymphocytes requires antiapoptotic MCL-1. Nature. 2003;426:671-6.
Pinkert et al., An albumin enhancer located 10 kb upstream functions along with its promoter to direct efficient, liver-specific expression in transgenic mice. Genes and Dev. 1987;1:268-276.
Polster et al., BH3 Death Domain Peptide Induces Cell Type-selective Mitochondrial Outer Membrane Permeability. J. Biol. Chem. 2001;276 (41):37887-94.
Presta, Antibody engineering. Curr. Op. Struct. Biol. 1992;2:593-6.
Putcha et al., Induction of BIM, a Proapoptotic Bh3-Only BCL-2 Family Member, Is Critical for Neuronal Apoptosis. Neuron. 2001;29(3):615-28.
Puthalakath et al., Bmf: a Proapoptotic BH3-Only Protein Regulated by Interaction with the Myosin V Actin Motor Complex, Activated by Anoikis. Science. 2001;293:1829-32.
Puthalakath et al., Keeping killers on a tight leash: transcriptional and post-translational control of the pro-apoptotic activity of BH3-only proteins. Cell Death Differ. 2002;9:505-12.
Puthalakath et al., The Proapoptotic Activity of the Bcl-2 Family Member Bim is Regulated by Interaction with the Dynein Motor Complex. Mol. Cell. 1999;3:287-96.
Raff, Social controls on cell survival and cell death. Nature. 1992;356:397-400.

(56) References Cited

OTHER PUBLICATIONS

Rassenti et al., ZAP-70 Compared with Immunoglobulin Heavy-Chain Gene Mutation Status as a predictor of Disease Progression in Chronic Lymphocytic Leukemia. N. Engl. J. Med. 2004;351:893-901.

Ray et al., BNIP3 Heterodimerizes with Bcl-2/Bcl-$X_L$ and Induces Cell Death Independent of a Bcl-2 Homology 3 (BH3) Domain at Both Mitochondrial and Nonmitochondrial Sites. J. Biol. Chem. 2000;275(2):1439-48.

Readhead et al., Expression of a myelin basic protein gene in transgenic shiverer mice: correction of the dysmyelinating phenotype. Cell. 1987;48:703-12.

Ren et al., BID, BIM, and PUMA Are Essential for Activation of the BAX- and BAK-Dependent Cell Death Program. Science. Dec. 2010;330:1390-3.

Riechmann et al., Reshaping human antibodies for therapy. Nature. 1988;332:323-7.

Rothbard et al., Conjugation of arginine oligomers to cyclosporine A facilitates topical delivery and inhibition of inflammation. Nature Med. 2000;6(11):1253-7.

Ryan et al., Heightened mitochondrial priming is the basis for apoptotic hypersensitivity of CD4+ CD8+ thymocytes. Proc Natl Acad Sci U S A. Jul. 20, 2010;107(29):12895-900. doi: 10.1073/pnas.0914878107. Epub Jul. 6, 2010.

Samson et al., A 35 amino acid fragment of leptin inhibits feeding in the rat. Endocrinology. 1996;137:5182-5.

Sattler et al., Structure of Bcl-x.sub.L-Bak Peptide Complex: Recognition Between Regulators of Apoptosis. Science. 1997;275:983-6.

Schimmer et al., Cell Death and Differentiation. 2001;8(7):725-33. Sequence Search Result.

Shalaby et al., Development of humanized bispecific antibodies reactive with cytotoxic lymphocytes and tumor cells overexpressing the HER2 protooncogene. Exp. Med. 1992;175:217-25.

Shangary et al., Peptides derived from BH3 domains of Bcl-2 family members: a comparative analysis of inhibition of Bcl-2, Bcl-x(L) and Bax oligomerization, induction of cytochrome c release, and activation of cell death. Biochemistry. Jul. 30, 2002;41(30):9485-95.

Shimizu et al., Proapoptotic BH3-only Bcl-2 family members induce cytochrome c release, but not mitochondrial membrane potential loss, and do not directly modulate voltage-dependent anion channel activity. Proc Natl Acad Sci U S A. Jan. 18, 2000;97(2):577-82.

Shopes, A genetically engineered human IgG mutant with enhanced cytolytic activity. J Immunol. 1992. 148:2918-2922.

Stevenson et al., A chimeric antibody with dual Fc regions (bisFabFc) prepared by manipulations at the IgG hinge. Anti-Cancer Drug Design. 1989;3:219-30.

Strupp et al., Treatment of Cells with Detergent Activates Caspases and Induces Apoptotic Cell Death. J. Membrane Biology. Jun. 2000;175(3): 181-9.

Suresh et al., Bispecific Monoclonal Antibodies from Hybrid Hybridomas. Methods in Enzymology. 1986;121:210-28.

Suzuki et al., Possible Existence of Common Internalization Mechanisms among Arginine-rich Peptides. J. Biol. Chem. 2002;277:2437-43.

Terradillos et al. FEBS. Lett. 2002;522(1-3):29-34.

Traunecker et al., Bispecific single chain molecules (Janusins) target cytotoxic lymphocytes on HIV infected cells. EMBO J. 1991;10:3655-9.

Tutt et al., Trispecific F(ab')3 derivatives that use cooperative signaling via the TCR/CD3 complex and CD2 to activate and redirect resting cytotoxic T cells. J. Immunol. 1991;147:60.

Vaux et al., Bcl-2 gene promotes haemopoietic cell survival and cooperates with c-myc to immortalize pre-B cells. Nature. 1988;335(6189):440-42.

Verhoeyen et al., Reshaping Human Antibodies: Grafting an Antilysozyme Activity. Science. 1988;239:1534-6.

Vieira et al., Cell permeable BH3-peptides overcome the cytoprotective effect of Bcl-2 and Bcl-XL. Oncogene. 2002 21:1963-77.

Vitetta et al., Redesigning Nature's Poisons to Create Anti-Tumor Reagents. Science. 1987;238:1098-104.

Vives et al., A Truncated HIV-1 Tat Protein Basic Domain Rapidly Translocates through the Plasma Membrane and Accumulates in the Cell Nucleus. J. Biol. Chem. 1997;272(25):16010-7.

Vo et al., Relative mitochondrial priming of myeloblasts and normal HSCs determines chemotherapeutic success in AML. Cell. Oct. 12, 2012;151(2):344-55.

Wang et al., Bid: A Novel BH3 Domain-Only Death Agonist. Genes Dev. 1996;10(22):2859-69.

Wang et al., Cell Permeable Bcl-2 binding Peptides: A Chemical Approach to Apoptosis Induction in Tumor Cells. Cancer Res. 2000;60:1498-502.

Wang et al., Structure based discovery of an organic compound that binds Bcl-2 protein and induces apoptosis of tumor cells. PNAS. 2000;97:7124-9.

Wang, The Expanding Role of Mitochondria in Apoptosis. Genes Dev. 2001;15:2922-33.

Wei et al., Proapoptotic BAX and BAK: A Requisite Gateway to Mitochondrial Dysfunction and Death. Science. 2001;292(5517):727-30.

Wei et al., tBID, a membrane-targeted death ligand, oligomerizes BAK to release cytochrome c. Genes & Development. 2000;14:2060-71.

Weinstein, Addiction to Oncogenes—the Achilles Heal of Cancer. Science. 2002;297:63-4.

Werner et al., Bcl-2 Family Member Bfl-1/A1 Sequesters Truncated Bid to Inhibit its Collaboration With Pro-Apoptotic Bak or Bax. J. Biol. Chem. 2002;277(25):22781-8.

Westerhoff et al., Magainins and the disruptioin of membrane-linked free-energy transduction. Proc. Natl. Acad. Sci. USA. Sep. 1989;86(17):6597-601.

Wilkinson, Immunochemical techniques inspire development of new antibody purification methods. The Scientist. 2000;14(8):25-8.

Willis et al., Apoptosis Initiated When BH3 Ligands Engage Multiple Bcl-2Homologs, not Bax or Bak. Science. Feb. 2007;315:856-9.

Willis et al., Proapoptotic Bak is sequestered by Mcl-1 and Bcl-xL, but not Bcl-2, until displaced by BH3-only proteins. Genes Dev. 2005;19:1294-305.

Wolff et al., Monoclonal antibody homodimers: Enhanced antitumor activity in Nude Mice. Cancer Research. 1993;53:2560-5.

Wolter et al., Movement of Bax from the Cytosol to Mitochondria during Apoptosis. J. Cell Biol. 1997;139(5):1281-92.

Yamaguchi et al., Bcl-XL Protects BimEL-induced Bax Conformational Change and Cytochrome c Release Independent of Interacting with Bax or BimEL. J. Biol. Chem. 2002;277(44):41604-12.

Yang et al., Bad, a Heterodimeric Partner for Bcl-X.sub.L and Bcl-2, Displaces Bax and Promotes Cell Death. Cell. 1995;80(2):285-91.

Yang et al., Calculation of Protein Conformation from Circular Dichroism. Methods Enzymol. 1986;130:208-69.

Yasuda et al., BNIP3 α: a Human Homolog of Mitochondrial Proapoptotic protein BNIP3. Cancer Res. 1999;59:533-7.

Yi et al., Inhibition of Bid-induced apoptosis by Bcl-2. tBid insertion, Bax translocation, and Bax/Bak oligomerization suppressed. J Biol Chem. May 9, 2003;278(19):16992-9. Epub Mar. 6, 2003.

Zha et al., BH3 Domain of BAD is Required for Heterodimerization with Bcl-X.sub.L and Pro-apoptotic Activity. J. Biol. Chem. 1997;272(39):24101-4.

Zha et al., Serine Phosphorylation of Death Agonist BAD in Response to Survival Factor Results in Binding to 14-3-3 Not BCL-X.sub.L. Cell. 1996;87:619-28.

Zha et al., Posttranslational N-Myristoylation of BID as a Molecular Switch for targeting Mitochondria and Apoptosis. Science. 2000;290(5497)1761-5.

Zhou et al., Novel mutant-selective EGFR kinase inhibitors against EGFR T790M. Nature. Dec. 24, 2009;462(7276):1070-4.

Zong et al., BH3-only proteins that bind pro-survival Bcl-2 family members fail to induce apoptosis in the absence of Bax and Bak. Genes & Development. 2001;15:1481-6.

(56) References Cited

OTHER PUBLICATIONS

Extended European Search Report for EP14845952.2 dated Mar. 27, 2017.
International Preliminary Report on Patentability for PCT/US2014/056284 dated Mar. 31, 2016.
International Search Report and Written Opinion for PCT/US2016/029495 dated Aug. 5, 2016.
International Search Report and Written Opinion for PCT/US2016/029510 dated Aug. 12, 2016.
Barretina et al., The Cancer Cell Line Encyclopedia enables predictive modelling of anticancer drug sensitivity. Nature. Mar. 28, 2012;483(7391):603-7. doi: 10.1038/nature11003. Erratum in: Nature. Dec. 13, 2012;492(7428):290.
Buron et al., Use of human cancer cell lines mitochondria to explore the mechanisms of BH3 peptides and ABT-737-induced mitochondrial membrane permeabilization. PLoS One. Mar. 31, 2010;5(3):e9924. doi:10.1371/journal.pone.0009924.
Friedman et al., Precision medicine for cancer with next-generation functional diagnostics. Nat Rev Cancer. Dec. 2015;15(12):747-56. doi: 10.1038/nrc4015. Epub Nov. 5, 2015.
Letai, Perturbing cancer cell mitochondria to learn how to kill cancer with BH3 profiling. Broad Institute, Seminar Series on Cell Circuits and Epigenomics. Jul. 28, 2014 Presentation.
Long et al., Optimization and validation of mitochondria-based functional assay as a useful tool to identify BH3-like molecules selectively targeting anti-apoptotic Bcl-2 proteins. BMC Biotechnol. May 24, 2013;13:45. doi: 10.1186/1472-6750-13-45.
Oliver et al., Permeabilization of Cell Membranes. C. Oliver and M.C. Jamur (eds.), Immunocytochemical Methods and Protocols, Methods in Molecular Biology, vol. 588, DOI 10.1007/978-1-59745-324-0_9, © Humana Press, a part of Springer Science + Business Media, LLC 1995, 1999, 2010. Chapter 9: 4 pages.
Ryan et al., BH3 profiling in whole cells by fluorimeter or FACS. Methods. Jun. 1, 2013;61(2):156-64. doi: 10.1016/j.ymeth.2013.04.006. Epub Apr. 20, 2013.
Sen et al., Artemisinin triggers induction of cell-cycle arrest and apoptosis in Leishmania donovani promastigotes. J Med Microbiol. Sep. 2007;56(Pt 9):1213-8.
Song et al., Carbon monoxide promotes Fas/CD95-induced apoptosis in Jurkat cells. J Biol Chem. Oct. 22, 2004;279(43):44327-34. Epub Jul. 27, 2004. Erratum in: J Biol Chem. Jun. 10, 2005;280(23):22555.
Sugiyama et al., Activation of mitochondrial voltage-dependent anion channel by a pro-apoptotic BH3-only protein Bim. Oncogene. Jul. 25, 2002;21(32):4944-56.
Vaquero et al., Extracellular matrix proteins protect pancreatic cancer cells from death via mitochondrial and nonmitochondrial pathways. Gastroenterology. Oct. 2003;125(4):1188-202.
International Preliminary Report on Patentability for PCT/US2016/029495 dated Nov. 9, 2017.
International Preliminary Report on Patentability for PCT/US2016/029510 dated Nov. 9, 2017.
Quinsay et al., Pro-Apoptotic Bnip3 Mediates Permeabilization of Mitochondria and Release of Cytocrome c via a Novel Mechanism. Circulation. Oct. 28, 2008;118(18):S388. Abstract.
Soltow et al., Overexpression of CuZnSOD or MnSOD protects satellite cells from doxorubicin-induced apoptosis. FASEB Journal. Apr. 2007;21:A449. Abstract.
U.S. Appl. No. 10/658,028, filed Sep. 9, 2003, Abandoned, 2004-0171809.
U.S. Appl. No. 11/789,557, filed Apr. 24, 2007, Granted, U.S. Pat. No. 7,868,133.
U.S. Appl. No. 12/966,821, filed Dec. 13, 2010, Published, 2011-0154522.
U.S. Appl. No. 15/073,356, filed Mar. 17, 2016, Pending.
U.S. Appl. No. 11/695,321, filed Apr. 2, 2007, Granted, U.S. Pat. No. 8,221,966.
U.S. Appl. No. 13/478,831, filed May 23, 2012, Published, 2013-0149718.
U.S. Appl. No. 15/073,391, filed Mar. 7, 2016, Pending.
U.S. Appl. No. 15/022,987, filed Mar. 18, 2016, Pending.
EP03749602.3, Jun. 7, 2006, Supplementary Partial European Search Report.
EP03749602.3, Sep. 28, 2006, Supplementary Partial European Search Report.
PCT/US2003/028482, Dec. 8, 2005, International Search Report.
PCT/US2007/008055, Jan. 2, 2008, International Search Report and Written Opinion.
PCT/US2007/008055, Sep. 30, 2008, International Preliminary Report on Patentability.
PCT/US2013/060707, Jan. 9, 2014, International Search Report and Written Opinion.
PCT/US2013/060707, Apr. 2, 2015, International Preliminary Report on Patentability.
PCT/US2014/056284, Dec. 31, 2014, International Search Report and Written Opinion.
U.S. Appl. No. 15/869,537, filed Jan. 12, 2018, Korsmeyer et al.
U.S. Appl. No. 15/568,994, filed Oct. 24, 2017, Letai et al.
U.S. Appl. No. 15/569,851, filed Oct. 27, 2017, Letai et al.
PCT/US2016/029495, Nov. 9, 2017, International Preliminary Report on Patentability.
PCT/US2016/029510, Nov. 9, 2017, International Preliminary Report on Patentability.
Campos et al., Method for monitoring of mitochondrial cytochrome c release during cell death: Immunodetection of cytochrome c by flow cytometry after selective permeabilization of the plasma membrane. Cytometry Part A. Jun. 2006;69(6):515-23.
Extended European Search Report for EP16787039.3 dated Oct. 4, 2018.
Extended European Search Report for EP16787045.0 dated Oct. 4, 2018.
EP16787039.3, Oct. 4, 2018, Extended European Search Report.
EP16787045.0, Oct. 4, 2018, Extended European Search Report.

* cited by examiner

A

B

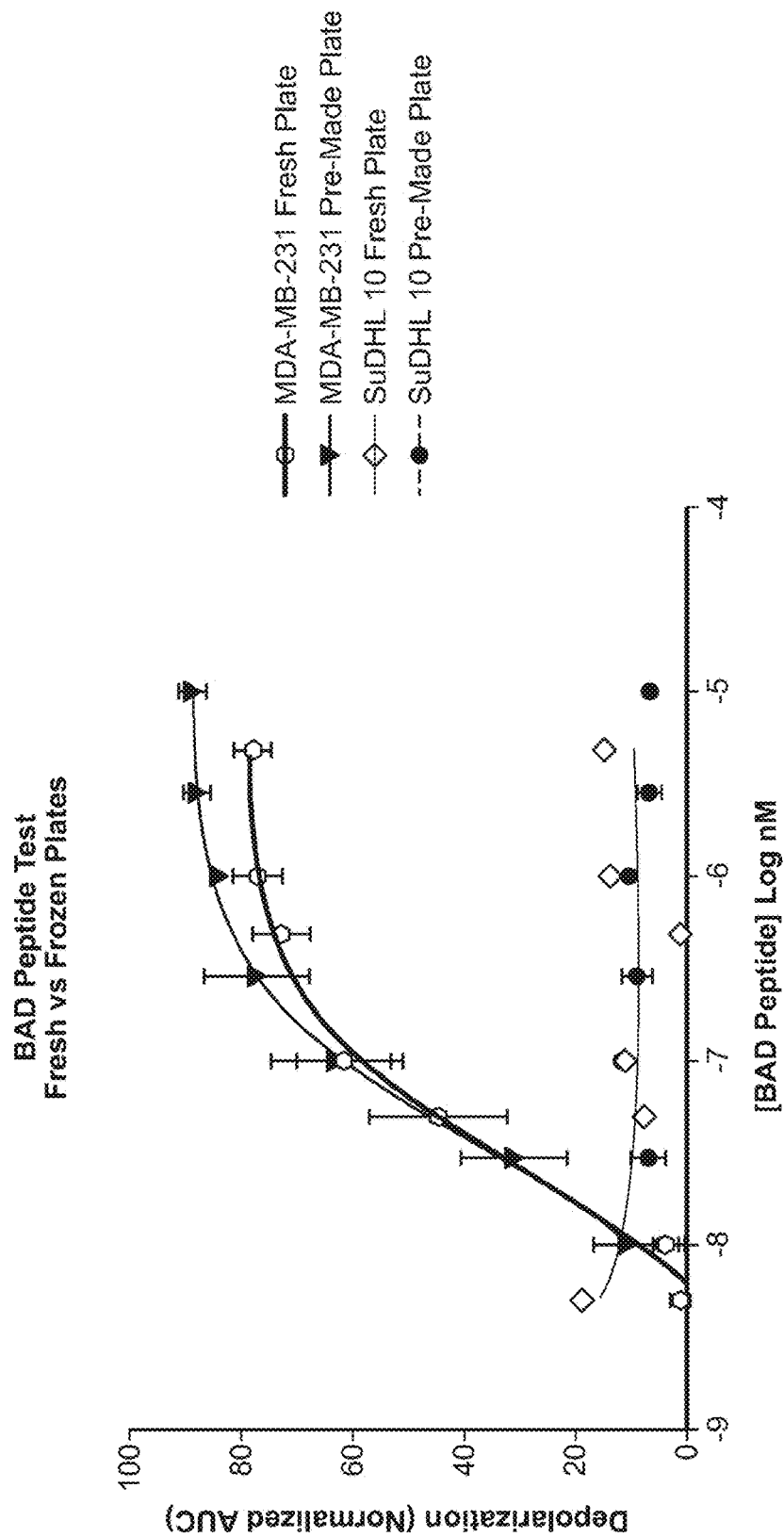

SEQUENCE LISTING

<160> NUMBER OF SEQ ID NOS: 16

<210> SEQ ID NO 1
<211> LENGTH: 20
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (20)..(20)
<223> OTHER INFORMATION: AMIDATED

<400> SEQUENCE: 1

Met Arg Pro Glu Ile Trp Ile Ala Gln Glu Leu Arg Arg Ile Gly Asp
1               5                   10                  15

Glu Phe Asn Ala
            20

<210> SEQ ID NO 2
<211> LENGTH: 20
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (20)..(20)
<223> OTHER INFORMATION: AMIDATED

<400> SEQUENCE: 2

Met Arg Pro Glu Ile Trp Ile Ala Gln Glu Leu Arg Arg Ile Gly Asp
1               5                   10                  15

Glu Phe Asn Val
            20

<210> SEQ ID NO 3
<211> LENGTH: 20
<212> TYPE: PRT
<213> ORGANISM: Artificial Sequence
<220> FEATURE:
<223> OTHER INFORMATION: Synthetic Polypeptide

<400> SEQUENCE: 3

Glu Asp Ile Ile Arg Asn Ile Ala Arg His Leu Ala Gln Val Gly Asp
1               5                   10                  15

Ser Met Asp Arg
            20

<210> SEQ ID NO 4
<211> LENGTH: 20
<212> TYPE: PRT
<213> ORGANISM: Artificial Sequence
<220> FEATURE:
<223> OTHER INFORMATION: Synthetic Polypeptide

<400> SEQUENCE: 4

Met Arg Pro Glu Ile Trp Ile Ala Gln Glu Leu Arg Arg Ile Gly Asp
1               5                   10                  15

```
Glu Phe Asn Ala
            20

<210> SEQ ID NO 5
<211> LENGTH: 20
<212> TYPE: PRT
<213> ORGANISM: Artificial Sequence
<220> FEATURE:
<223> OTHER INFORMATION: Synthetic Polypeptide

<400> SEQUENCE: 5

Glu Asp Ile Ile Arg Asn Ile Ala Arg His Ala Ala Gln Val Gly Ala
1               5                   10                  15

Ser Met Asp Arg
            20

<210> SEQ ID NO 6
<211> LENGTH: 25
<212> TYPE: PRT
<213> ORGANISM: Artificial Sequence
<220> FEATURE:
<223> OTHER INFORMATION: Synthetic Polypeptide

<400> SEQUENCE: 6

Leu Trp Ala Ala Gln Arg Tyr Gly Arg Glu Leu Arg Arg Met Ser Asp
1               5                   10                  15

Glu Phe Glu Gly Ser Phe Lys Gly Leu
            20                  25

<210> SEQ ID NO 7
<211> LENGTH: 20
<212> TYPE: PRT
<213> ORGANISM: Artificial Sequence
<220> FEATURE:
<223> OTHER INFORMATION: Synthetic Polypeptide

<400> SEQUENCE: 7

Met Glu Gly Ser Asp Ala Leu Ala Leu Arg Leu Ala Cys Ile Gly Asp
1               5                   10                  15

Glu Met Asp Val
            20

<210> SEQ ID NO 8
<211> LENGTH: 20
<212> TYPE: PRT
<213> ORGANISM: Artificial Sequence
<220> FEATURE:
<223> OTHER INFORMATION: Synthetic Polypeptide

<400> SEQUENCE: 8

Ala Glu Leu Pro Pro Glu Phe Ala Ala Gln Leu Arg Lys Ile Gly Asp
1               5                   10                  15

Lys Val Tyr Cys
            20

<210> SEQ ID NO 9
<211> LENGTH: 20
<212> TYPE: PRT
<213> ORGANISM: Artificial Sequence
<220> FEATURE:
<223> OTHER INFORMATION: Synthetic Polypeptide

<400> SEQUENCE: 9

Pro Ala Asp Leu Lys Asp Glu Cys Ala Gln Leu Arg Arg Ile Gly Asp
1               5                   10                  15
```

Lys Val Asn Leu
            20

<210> SEQ ID NO 10
<211> LENGTH: 20
<212> TYPE: PRT
<213> ORGANISM: Artificial Sequence
<220> FEATURE:
<223> OTHER INFORMATION: Synthetic Polypeptide

<400> SEQUENCE: 10

Ser Ser Ala Ala Gln Leu Thr Ala Ala Arg Leu Lys Ala Leu Gly Asp
1               5                   10                  15

Glu Leu His Gln
            20

<210> SEQ ID NO 11
<211> LENGTH: 20
<212> TYPE: PRT
<213> ORGANISM: Artificial Sequence
<220> FEATURE:
<223> OTHER INFORMATION: Synthetic Polypeptide

<400> SEQUENCE: 11

Glu Gln Trp Ala Arg Glu Ile Gly Ala Gln Leu Arg Arg Met Ala Asp
1               5                   10                  15

Asp Leu Asn Ala
            20

<210> SEQ ID NO 12
<211> LENGTH: 20
<212> TYPE: PRT
<213> ORGANISM: Artificial Sequence
<220> FEATURE:
<223> OTHER INFORMATION: Synthetic Polypeptide

<400> SEQUENCE: 12

His Gln Ala Glu Val Gln Ile Ala Arg Lys Leu Gln Leu Ile Ala Asp
1               5                   10                  15

Gln Phe His Arg
            20

<210> SEQ ID NO 13
<211> LENGTH: 25
<212> TYPE: PRT
<213> ORGANISM: Artificial Sequence
<220> FEATURE:
<223> OTHER INFORMATION: Synthetic Polypeptide

<400> SEQUENCE: 13

Asn Leu Trp Ala Ala Gln Arg Tyr Gly Arg Glu Leu Arg Arg Met Ser
1               5                   10                  15

Asp Glu Phe Val Asp Ser Phe Lys Lys
            20                  25

<210> SEQ ID NO 14
<211> LENGTH: 25
<212> TYPE: PRT
<213> ORGANISM: Artificial Sequence
<220> FEATURE:
<223> OTHER INFORMATION: Synthetic Polypeptide

<400> SEQUENCE: 14

Leu Trp Ala Ala Gln Arg Tyr Gly Arg Glu Ala Arg Arg Met Ser Asp

-continued

```
                1               5                      10                      15
Glu Phe Glu Gly Ser Phe Lys Gly Leu
                        20                      25

<210> SEQ ID NO 15
<211> LENGTH: 20
<212> TYPE: PRT
<213> ORGANISM: Artificial Sequence
<220> FEATURE:
<223> OTHER INFORMATION: Synthetic Polypeptide

<400> SEQUENCE: 15

Glu Gln Trp Ala Arg Glu Ile Gly Ala Gln Ala Arg Arg Met Ala Ala
1               5                      10                      15

Asp Leu Asn Ala
            20

<210> SEQ ID NO 16
<211> LENGTH: 20
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (1)..(10)
<223> OTHER INFORMATION: Xaa can be any naturally occurring amino acid
<220> FEATURE:
<221> NAME/KEY: misc_feature
<222> LOCATION: (12)..(15)
<223> OTHER INFORMATION: Xaa can be any naturally occurring amino acid
<220> FEATURE:
<221> NAME/KEY: misc_feature
<222> LOCATION: (17)..(20)
<223> OTHER INFORMATION: Xaa can be any naturally occurring amino acid

<400> SEQUENCE: 16

Xaa Xaa Xaa Xaa Xaa Xaa Xaa Xaa Xaa Xaa Leu Xaa Xaa Xaa Xaa Asp
1               5                      10                      15

Xaa Xaa Xaa Xaa
            20
```

DYNAMIC BH3 PROFILING

RELATED APPLICATIONS

This application claims priority to and benefit of provisional application U.S. Ser. No. 61/702,967 filed on Sep. 19, 2012, the contents of which are herein incorporated by reference in its entirety.

FIELD OF INVENTION

The invention relates to generally to methods of predicting response to chemotherapy and in particular targeted therapies.

BACKGROUND OF THE INVENTION

As more targeted therapies are approved for different types of cancer, there is a growing need for predictive biomarkers so that these therapies can be directed to patients who will most benefit from them; unfortunately, the biomarkers available for cancer therapy are not sufficient. Recently, the development of tyrosine kinase inhibitors (TKI) improved treatment in patients with advanced disease. For example, detection of mutations in EGFR has been successfully used as a biomarker for initial therapy with EGFR inhibitors. Many targeted agents lack genetic predictive biomarkers. Furthermore, resistance to these drugs frequently emerges, and it is often not clear what treatment is best given following this emergence of resistance, given the variety of mechanisms for resistance. The present invention provides a method of predicting the response to therapy so that drugs can better be assigned to patients.

SUMMARY OF THE INVENTION

In various aspects, the invention provides methods of predicting the response to chemotherapy.

In various aspects the invention provides methods of predicting sensitivity of a cell to a therapeutic agent by contacting a test cell population that has been exposed to a test therapeutic agent with a pro-apoptotic BH3 domain peptide, measuring the amount of BH3 domain peptide induced mitochondrial outer membrane permeabilization in the test cell population and comparing the amount of BH3 domain peptide induced mitochondrial outer membrane permeabilization in the test cell population to a control cell population that has not been contacted with the therapeutic agent. An increase in mitochondrial sensitivity to a BH3 domain peptide in the test cell population compared to the control cell population indicates the cell is sensitive to the therapeutic agent. In various embodiments the cell is permeabilized prior to contacting with the BH3 domain peptide. In various aspects, the method further comprises contacting the permeabilized cell with a potentiometric dye. Potentiometric dyes include for example JC-1 or dihydrorhodamine 123.

Mitochondrial outer membrane permeabilization is determined for example by measuring i) the emission of a potentiometric or radiometric dye or ii) the release of molecules from the mitochondrial inter-membrane space.

BH3 domain peptides include peptides derived from the BH3 domain of a BID, a BIM, a BAD, a NOXA, a PUMA, a BMF, or a HRK polypeptide. Exemplary BH3 domain peptides include SEQ ID NO: 1-14

The therapeutic agent is a chemotherapeutic agent such as a kinase inhibitor.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the claims.

BRIEF DESCRIPTION OF THE DRAWINGS

FIG. 15 is a graph showing that pre-made frozen plates perform the same as freshly prepared plates. Responsive cells (MDA-MB-231) show comparable response to a peptide treatment (BAD) in both frozen and freshly prepared plates. Non-responsive cells (SuDHL10) are used to test for non-specific noise, and frozen plates produce a response equivalent to freshly prepared plates.

DETAILED DESCRIPTION OF THE INVENTION

Figure 1:
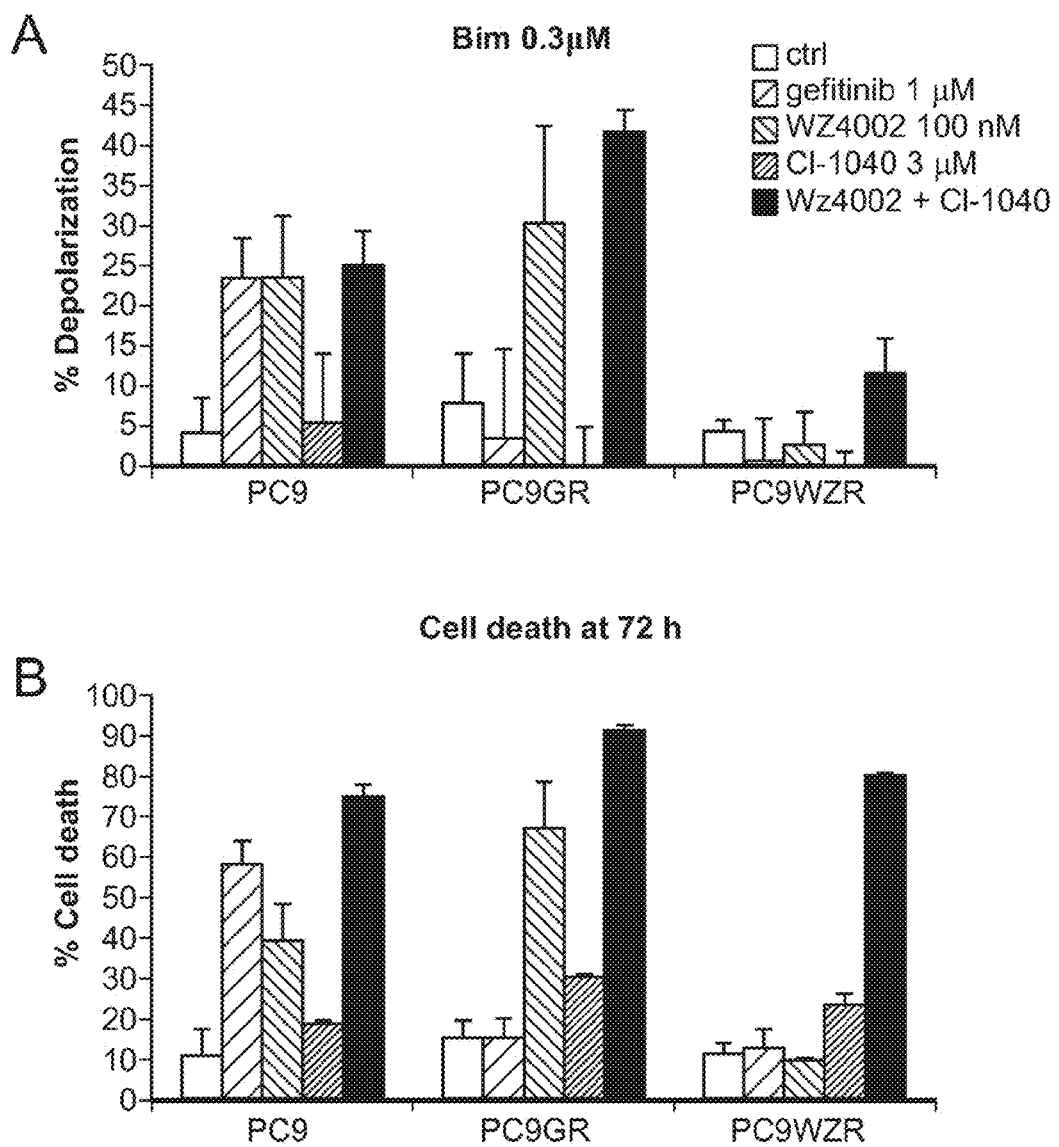
FIG. 1. Dynamic BH3 profiling in NSCLC cell lines PC9, PC9GR and PC9WZR. (A) BH3 profiling results on cells exposed to drug for 16 h, using mitochondrial response to the Bim peptide (0.3 µM) response to measure priming. (B) Cell death was measured at 72 h by FACS using Annexin V/PI staining.

The present invention is based in part on the discovery of a technique that measures how close a cancer cell is to the threshold of programmed cell death (i.e. apoptosis), also known as measuring how "primed" the cancer cell is for death. The methods of the invention allow the identification of drugs that move cancer cells closer to the threshold of programmed cell death (increase priming the most). This invention can be applied to individual clinical cancer samples, so that those drugs that move the cells in that sample closest to the threshold of programmed cell death for that individual sample can be readily identified. The drugs so identified are those most likely to provide clinical benefit to the subject from which the sample was derived. Therefore the invention provides a method of personalizing therapy for individual cancer patients.

This technique differs from previous techniques described in US2008/0199890 in that the method of the present invention allows for the observation of the dynamic effects of any number of individual drugs or combination thereof on the mitochondrial priming of an individual cancer sample. The previous method solely measured the priming of a cancer sample at baseline, unperturbed by any panel of chemical agents. Those cells that were closest to the apoptotic threshold were therefore most primed for death and were predicted to be most responsive to chemotherapy generally, but without the ability to discriminate to which agent a cell was most likely to be most sensitive. In contrast, the method of this invention allows the change in priming attributed to a particular drug to be assessed, thus determining whether the compound causes the cell to move closer to the apoptotic threshold. Moreover, the methods of the invention are superior to previous methods as it is capable of determining whether a particular cell has become resistant to a particular therapeutic agent. The methods of the invention are referred to herein as Dynamic BH3 Profiling.

Dynamic BH3 Profiling

In various methods, sensitivity of a cell to an agent is determined. The methods include contacting a test cell with a test agent. Cell sensitivity to the test agent is determined by contacting the test cell or test cellular component (e.g., mitochondria) exposed to the test agent with standardized concentration of a panel of BH3 domain peptide from the pro-apoptotic BCL-2 family. Pro-apoptotic BCL-2 BH3 proteins and peptides include: Bcl-2 interacting mediator of cell death (BIM); a mutant thereof (BIM AV); BH3 interacting domain death agonist (BID); Bcl-2-associated death promoter (BAD); NOXA; p53 up-regulated modulator of apoptosis (PUMA); Bcl-2-modifying factor (BMF) and harakiri (HRK) (See, Table 1). The ability of BH3 peptides to induce mitochondrial outer membrane permeabilization is measured in the test population (i.e. cell or cellular component (e.g., mitochondria) and the control population (i.e. cell or cellular component (e.g., mitochondria) not exposed to the test agent. An increase in BH3 peptide-induced mitochondrial outer membrane permeabilization in the test population compared to the control population indicates that the cells will be responsive (i.e., cell death will be induced) to the test agent. Alternatively, no change (or a decrease) in mitochondrial outer membrane permeabilization in the test population compared to the control population indicates that the cells will be resistant (i.e. cell death will be induced) to the test agent.

The cell or cellular component is a cancer cell or a cell that is suspected of being cancerous. The cell is permeabilized to permit the BH3 peptides access to the mitochondria. Cells are permeabilized by methods known in the art. For example, the cell are permeabilized by contacting the cell with digitonin, or other art-recognized detergents and cell-permeabilization agents.

After the cells are permeabilized the cells are treated with the BH3 peptides or test agents. After the cell is treated, mitochondrial outer membrane permeabilization is measured. Outer membrane permeabilization is measured by a number of methods. For example outer membrane permeabilization is measured by loss of mitochondrial membrane potential. Loss of mitochondrial membrane potential is measured for example by treating the cells with a potentiometric or radiometric dye.

Alternatively, outer membrane permeabilization is determined by measuring the release of molecules from the mitochondrial inter-membrane space. Examples of molecules that can be measured include cytochrome c and SMAC/Diablo, Omi, adenylate kinase-2 or apoptotic-inducing factor (AIF). Optionally, the cells are fixed prior to measuring outer membrane permeabilization. Cells are fixed by methods known in the art such as by using an aldehyde such as formaldehyde.

Mitochondrial outer membrane permeabilization can be measured at the single cell level or multi-cell level. Additionally, some of the methods disclosed herein allow for subpopulations of cells to be assayed.

Examples of potentiometric dyes include the fluorescent JC-1 probe (5,5',6,6'-tetrachloro-1,1',3,3'-tetraethylbenzimidazolylcarbocyanine iodide) or dihydrorhodamine 123, or tetramethylrhodamine methyl ester (TMRM) or tetramethylrhodamine ethyl ester (TMRE)

JC-1 is a lipophilic, cationic dye that enters mitochondria in proportion to the potential across the inner mitochondrial membrane. JC-1 exists as a monomer at low membrane concentrations). However, JC-1 accumulates in the mitochondrial matrix under conditions of higher mitochondrial potentials. At these higher concentrations, JC-1 forms red-fluorescent "J-aggregates". As a monomer the dye has an absorption/emission maxima of 527 nm while at high membrane potential the emission maximum is 590 nm. Thus, ratio measurements of the emission of this cyanine dye can be used as a sensitive measure of mitochondrial membrane potential. The dye allows for a dual measurement of dye concentration that does not require the measurement of a nuclear or cytoplasmic reference value. Studies using isolated mitochondria have shown that the 527 nm emission from monomeric JC-1 increases almost linearly with membrane (M) potentials ranging from 46 to 182 mV, whereas the 590 nm J-aggregate emission is less sensitive to M values less negative than 140 my and is strongly sensitive to potential values in the range of 140 to 182 mV (Di Lisa et al., 1995). Optical filters designed for fluorescein and tetramethylrhodamine can be used to separately visualize the monomer and J-aggregate forms, respectively. Alternatively, both forms can be observed simultaneously using a standard fluorescein longpass optical filter set.

Dihydrorhodamine 123 is an uncharged, nonfluorescent agent that can be converted by oxidation to the fluorescent laser dye rhodamine 123 (R123).

Release of molecules from the mitochondrial inter-membrane space can be measured by methods known in the art. For example, by using antibodies to the molecules to be measured, i.e., antibodies to cytochrome c, SMAC/Diablo, Omi, adenylate kinase-2 or apoptotic-inducing factor (AIF). Detection can be for example, by ELISA, FACS, immunoblot, immunofluorescence, or immunohistochemistry.

In addition to measuring molecules that get released from the mitochondrial space, other intracellular and extracellular markers can be measured. This allows for the ability to discriminate between subpopulations of cells.

Dynamic BH3 profiling can be accomplished at the single cell level by immobilizing cells on a solid surface. Optionally the solid surface is polyamine or poly-lysine coated. Immobilized cells are permeabilized as described above. The cells are then contacted with BH3 peptides and/or test agents. After the cells have been treated for a predetermined period of time such as 45-90 minutes, the cells are fixed and permeabilized by methods known in the art. For example the cells are fixed with formaldehyde and further permeabilized with methanol or triton x-100. Outer membrane permeabilization is determined by intracellular staining for molecules from the mitochondrial inter-membrane space and a mitochondrial marker. Examples of molecules that can be measured include cytochrome c, SMAC/Diablo, Omi, adenylate kinase-2 or apoptotic-inducing factor (AIF). Mitochondrial markers include MnSOD. Stained cells can be counter-stained with nuclear stains such as DAPI. Optionally other intracellular and extracellular markers can be measured. Analysis of the cells can be manually accomplished using a microscope or automated for example by using software such as Cellprofiler to locate nuclei.

The cell is from a subject known to have or suspected of having cancer. The subject is preferably a mammal. The mammal is, e.g., a human, non-human primate, mouse, rat, dog, cat, horse, or cow. The subject has been previously diagnosed as having cancer, and possibly has already undergone treatment for cancer. Alternatively, the subject has not been previously diagnosed as having cancer.

The agent is a therapeutic agent such as a chemotherapeutic agent. For example, the agent a targeted chemotherapeutic agent such as a kinase inhibitor. One skilled in the art will appreciate that an agent can be screened for toxicity by the methods of the invention.

Apoptosis, i.e., cell death is identified by known methods. For example, cells shrink, develop bubble-like blebs on their surface, have the chromatin (DNA and protein) in their nucleus degraded, and have their mitochondria break down with the release of cytochrome c, loss of mitochondrial membrane potential, break into small, membrane-wrapped, fragments, or phosphatidylserine, which is normally hidden within the plasma membrane, is exposed on the surface of the cell.

The difference in the level of mitochondrial permeabilization induced by a BH3 peptide of a cell that has been contacted with a test agent compared to a cell that has not been contacted with the test agent is statistically significant. By statistically significant it is meant that the alteration is greater than what might be expected to happen by chance alone. Statistical significance is determined by method known in the art. For example statistical significance is determined by p-value. The p-value is a measure of probability that a difference between groups during an experiment happened by chance. ($P(z \geq z_{observed})$). For example, a p-value of 0.01 means that there is a 1 in 100 chance the result occurred by chance. The lower the p-value, the more likely it is that the difference between groups was caused by treatment. An alteration is statistically significant if the p-value is or less than 0.05. Preferably, the p-value is 0.04, 0.03, 0.02, 0.01, 0.005, 0.001 or less.

Pro-Apoptotic BCL-2 BH3 Domain Peptides

A Pro-apoptotic BCL-2 BH3 domain peptide is less than 195 amino acids in length, e.g., less than or equal to 150, 100, 75, 50, 35, 25 or 15 amino acid in length. Pro-apoptotic BCL-2 BH3 domain peptides include Bcl-2 interacting mediator of cell death (BIM); BH3 interacting domain death agonist (BID); Bcl-2-associated death promoter (BAD); NOXA; p53 up-regulated modulator of apoptosis (PUMA); Bcl-2-modifying factor (BMF) and harakiri (HRK). A BH3 domain peptide include a peptide which includes (in whole or in part) the sequence NH2-XXXXXXXXXX-LXXXXDXXXX-COOH (SEQ ID NO:16). As used herein X may be any amino acid. Alternatively. The BH3 domain peptides include at least 5, 6, 7, 8, 9, 15 or more amino acids of SEQ ID NO:16).

For example a Pro-apoptotic BCL-2 BH3 domain peptide includes the sequence of SEQ ID NO: 1-14 shown in Table 1. PUMA2A (SEQ ID NO: 15) is a negative control peptide.

TABLE 1

| BIM | Ac-MRPEIWIAQELRRIGDEFNA-NH2 | SEQ ID NO: 1 |
|---|---|---|
| BIM | Ac-MRPEIWIAQELRRIGDEFNV-NH2 | SEQ ID NO: 2 |
| BID | EDIIRNIARHLAQVGDSMDR | SEQ ID NO: 3 |
| BIM AV | MRPEIWIAQELRRIGDEFNA | SEQ ID NO: 4 |
| BID mut | EDIIRNIARHAAQVGASMDR | SEQ ID NO: 5 |
| BAD | LWAAQRYGRELRRMSDEFEGSFKGL | SEQ ID NO: 6 |
| BIK | MEGSDALALRLACIGDEMDV | SEQ ID NO: 7 |
| NOXA A | AELPPEFAAQLRKIGDKVYC | SEQ ID NO: 8 |
| NOXA B | PADLKDECAQLRRIGDKVNL | SEQ ID NO: 9 |
| HRK | SSAAQLTAARLKALGDELHQ | SEQ ID NO: 10 |
| PUMA | EQWAREIGAQLRRMADDLNA | SEQ ID NO: 11 |
| BMF | HQAEVQIARKLQLIADQFHR | SEQ ID NO: 12 |
| huBAD | NLWAAQRYGRELRRMSDEFVDSFKK | SEQ ID NO: 13 |
| BAD mut | LWAAQRYGREARRMSDEFEGSFKGL | SEQ ID NO: 14 |
| PUMA2A | EQWAREIGAQARRMAADLNA | SEQ ID NO: 15 |

The BH3 domain peptides can be modified using standard modifications. Modifications may occur at the amino (N-), carboxy (C-) terminus, internally or a combination of any of the preceding. In one aspect described herein, there may be more than one type of modification on the polypeptide. Modifications include but are not limited to: acetylation, amidation, biotinylation, cinnamoylation, farnesylation, formylation, myristoylation, palmitoylation, phosphorylation (Ser, Tyr or Thr), stearoylation, succinylation, sulfurylation and cyclisation (via disulfide bridges or amide cyclisation), and modification by Cys3 or Cys5. The GCRA peptides described herein may also be modified by 2,4-dinitrophenyl (DNP), DNP-lysine, modification by 7-Amino-4-methyl-coumarin (AMC), flourescein, NBD (7-Nitrobenz-2-Oxa-1,3-Diazole), p-nitro-anilide, rhodamine B, EDANS (5-((2-aminoethyl)amino)naphthalene-1-sulfonic acid), dabcyl, dabsyl, dansyl, texas red, FMOC, and Tamra (Tetramethylrhodamine).

Optionally, the BH3 domain peptide is attached to a transduction domain. A transduction domain directs a peptide in which it is present to a desired cellular destination. Thus, the transduction domain can direct the peptide across the plasma membrane, e.g., from outside the cell, through the plasma membrane, and into the cytoplasm. Alternatively, or in addition, the transduction domain can direct the peptide to a desired location within the cell, e.g., the nucleus, the ribosome, the ER, mitochondria, a lysosome, or peroxisome.

In some embodiments, the transduction domain is derived from a known membrane-translocating sequence. Alternatively, the transduction domain is a compound that is known to facilitate membrane uptake such as polyethylene glycol, cholesterol moieties, octanoic acid and decanoic acid.

For example, the trafficking peptide may include sequences from the human immunodeficiency virus (HIV) 1 TAT protein. This protein is described in, e.g., U.S. Pat. Nos. 5,804,604 and 5,674,980, each incorporated herein by reference. The BH3 domain peptide is linked to some or all of the entire 86 amino acids that make up the TAT protein. For example, a functionally effective fragment or portion of a TAT protein that has fewer than 86 amino acids, which exhibits uptake into cells can be used. See e.g., Vives et al., J. Biol. Chem., 272(25):16010-17 (1997), incorporated herein by reference in its entirety. A TAT peptide that includes the region that mediates entry and uptake into cells can be further defined using known techniques. See, e.g., Franked et al., Proc. Natl. Acad. Sci, USA 86: 7397-7401 (1989). Other sources for translocating sequences include, e.g., VP22 (described in, e.g., WO 97/05265; Elliott and O'Hare, Cell 88: 223-233 (1997)), Drosophila Antennapedia (Antp) homeotic transcription factor, HSV, poly-arginine, poly lysine, or non-viral proteins (Jackson et al, Proc. Natl. Acad. Sci. USA 89: 10691-10695 (1992)).

The transduction domain may be linked either to the N-terminal or the C-terminal end of the BH3 domain peptide. A hinge of two proline residues may be added between the transduction domain and BH3 domain peptide to create the full fusion peptide. Optionally, the transduction domain is linked to the BH3 domain peptide in such a way that the transduction domain is released from the BH3 domain peptide upon entry into the cell or cellular component.

The transduction domain can be a single (i.e., continuous) amino acid sequence present in the translocating protein. Alternatively it can be two or more amino acid sequences, which are present in protein, but are separated by other amino acid sequences in the naturally-occurring protein.

The amino acid sequence of naturally-occurring translocation protein can be modified, for example, by addition, deletion and/or substitution of at least one amino acid present in the naturally-occurring protein, to produce modified protein. Modified translocation proteins with increased or decreased stability can be produced using known techniques. In some embodiments, translocation proteins or peptides include amino acid sequences that are substantially similar, although not identical, to that of the naturally-occurring protein or portions thereof. In addition, cholesterol or other lipid derivatives can be added to translocation protein to produce a modified protein having increased membrane solubility.

The BH3 domain peptide and the transduction domain can be linked by chemical coupling in any suitable manner known in the art. Many known chemical cross-linking methods are non-specific, i.e., they do not direct the point of coupling to any particular site on the transport polypeptide or cargo macromolecule. As a result, use of non-specific cross-linking agents may attack functional sites or sterically block active sites, rendering the conjugated proteins biologically inactive.

One way to increase coupling specificity is to directly chemically couple to a functional group found only once or a few times in one or both of the polypeptides to be cross-linked. For example, in many proteins, cysteine, which is the only protein amino acid containing a thiol group, occurs only a few times. Also, for example, if a polypeptide contains no lysine residues, a cross-linking reagent specific for primary amines will be selective for the amino terminus of that polypeptide. Successful utilization of this approach to increase coupling specificity requires that the polypeptide have the suitably rare and reactive residues in areas of the molecule that may be altered without loss of the molecule's biological activity.

Cysteine residues may be replaced when they occur in parts of a polypeptide sequence where their participation in a cross-linking reaction would otherwise likely interfere with biological activity. When a cysteine residue is replaced, it is typically desirable to minimize resulting changes in polypeptide folding. Changes in polypeptide folding are minimized when the replacement is chemically and sterically similar to cysteine. For these reasons, serine is preferred as a replacement for cysteine. As demonstrated in the examples below, a cysteine residue may be introduced into a polypeptide's amino acid sequence for cross-linking purposes. When a cysteine residue is introduced, introduction at or near the amino or carboxy terminus is preferred. Conventional methods are available for such amino acid sequence modifications, whether the polypeptide of interest is produced by chemical synthesis or expression of recombinant DNA.

Coupling of the two constituents can be accomplished via a coupling or conjugating agent. There are several intermolecular cross-linking reagents which can be utilized, See for example, Means and Feeney, Chemical Modification of Proteins, Holden-Day, 1974, pp. 39-43. Among these reagents are, for example, J-succinimidyl 3-(2-pyridyldithio) propionate (SPDP) or N,N'-(1,3-phenylene) bismaleimide (both of which are highly specific for sulfhydryl groups and form irreversible linkages); N, N'-ethylene-bis-(iodoacetamide) or other such reagent having 6 to 11 carbon methylene bridges (which relatively specific for sulfhydryl groups); and 1,5-difluoro-2,4-dinitrobenzene (which forms irreversible linkages with amino and tyrosine groups). Other cross-linking reagents useful for this purpose include: p,p'-difluoro-m,m'-dinitrodiphenylsulfone (which forms irreversible cross-linkages with amino and phenolic groups); dimethyl adipimidate (which is specific for amino groups); phenol-1,4-disulfonylchloride (which reacts principally with amino groups); hexamethylenediisocyanate or diisothiocyanate, or azophenyl-p-diisocyanate (which reacts principally with amino groups); glutaraldehyde (which reacts with several different side chains) and disdiazobenzidine (which reacts primarily with tyrosine and histidine).

Cross-linking reagents may be homobifunctional, i.e., having two functional groups that undergo the same reaction. A preferred homobifunctional cross-linking reagent is bismaleimidohexane ("BMH"). BMH contains two maleimide functional groups, which react specifically with sulfhydryl-containing compounds under mild conditions (pH 6.5-7.7). The two maleimide groups are connected by a hydrocarbon chain. Therefore, BMH is useful for irreversible cross-linking of polypeptides that contain cysteine residues.

Cross-linking reagents may also be heterobifunctional. Heterobifunctional cross-linking agents have two different functional groups, for example an amine-reactive group and a thiol-reactive group, that will cross-link two proteins having free amines and thiols, respectively. Examples of heterobifunctional cross-linking agents are succinimidyl 4-(N-maleimidomethyl) cyclohexane-1-carboxylate ("SMCC"), m-maleimidobenzoyl-N-hydroxysuccinimide ester ("MBS"), and succinimide 4-(p-maleimidophenyl) butyrate ("SMPB"), an extended chain analog of MBS. The succinimidyl group of these cross-linkers reacts with a primary amine, and the thiol-reactive maleimide forms a covalent bond with the thiol of a cysteine residue.

Cross-linking reagents often have low solubility in water. A hydrophilic moiety, such as a sulfonate group, may be added to the cross-linking reagent to improve its water solubility. Sulfo-MBS and sulfo-SMCC are examples of cross-linking reagents modified for water solubility.

Many cross-linking reagents yield a conjugate that is essentially non-cleavable under cellular conditions. However, some cross-linking reagents contain a covalent bond, such as a disulfide, that is cleavable under cellular conditions. For example, Traut's reagent, dithiobis (succinimidylpropionate) ("DSP"), and N-succinimidyl 3-(2-pyridyldithio) propionate ("SPDP") are well-known cleavable cross-linkers. The use of a cleavable cross-linking reagent permits the cargo moiety to separate from the transport polypeptide after delivery into the target cell. Direct disulfide linkage may also be useful.

Numerous cross-linking reagents, including the ones discussed above, are commercially available. Detailed instructions for their use are readily available from the commercial suppliers. A general reference on protein cross-linking and conjugate preparation is: Wong, Chemistry Of Protein Conjugation And Cross-Linking, CRC Press (1991).

Chemical cross-linking may include the use of spacer arms. Spacer arms provide intramolecular flexibility or adjust intramolecular distances between conjugated moieties and thereby may help preserve biological activity. A spacer arm may be in the form of a polypeptide moiety that includes spacer amino acids, e.g. proline. Alternatively, a spacer arm may be part of the cross-linking reagent, such as in "long-chain SPDP" (Pierce Chem. Co., Rockford, Ill., cat. No. 21651 H).

The BH3 domain peptides and/or the transduction domain peptides can be polymers of L-amino acids, D-amino acids, or a combination of both. For example, in various embodiments, the peptides are D retro-inverso peptides. The term "retro-inverso isomer" refers to an isomer of a linear peptide in which the direction of the sequence is reversed and the chirality of each amino acid residue is inverted. See, e.g., Jameson et al., Nature, 368, 744-746 (1994); Brady et al., Nature, 368, 692-693 (1994). The net result of combining D-enantiomers and reverse synthesis is that the positions of carbonyl and amino groups in each amide bond are exchanged, while the position of the side-chain groups at each alpha carbon is preserved. Unless specifically stated otherwise, it is presumed that any given L-amino acid sequence of the invention may be made into a D retro-inverso peptide by synthesizing a reverse of the sequence for the corresponding native L-amino acid sequence.

Alternatively, the BH3 domain peptides and/or the transduction domain peptides are cyclic peptides. Cyclic peptides are prepared by methods known in the art. For example, macrocyclization is often accomplished by forming an amide bond between the peptide N- and C-termini, between a side chain and the N- or C-terminus [e.g., with K3Fe(CN)6 at pH 8.5] (Samson et al., Endocrinology, 137: 5182-5185 (1996)), or between two amino acid side chains. See, e.g., DeGrado, Adv Protein Chem, 39: 51-124 (1988).

BH3 domain peptides and/or the transduction domain peptides are easily prepared using modern cloning techniques, or may be synthesized by solid state methods or by site-directed mutagenesis. A BH3 domain peptide and/or the transduction domain peptides may include dominant negative forms of a polypeptide. In one embodiment, native BH3 domain peptides and/or transduction domain peptides can be isolated from cells or tissue sources by an appropriate purification scheme using standard protein purification techniques. In another embodiment, BH3 domain polypeptides and/or transduction domain peptides are produced by recombinant DNA techniques. Alternative to recombinant expression, BH3 domain peptides and/or transduction domain peptides can be synthesized chemically using standard peptide synthesis techniques.

In various embodiments, the BH3 peptide maintains its secondary structure, e.g. a-helical structure. Methods of helix stabilization are known in the art.

Preferably, the BH3 peptide is a stable peptide. By "stable" it is meant that the peptide possess stability sufficient to allow the manufacture and which maintains the integrity of the compound for a sufficient period of time to be useful for the purposes detailed herein. For example the peptides are covalently stabilized suing polar and or labile crosslinks (Phelan et al. 1997 J. Am. Chem. Soc. 119:455; Leuc et al. 2003 Proc. Nat'l. Acad. Sci. USA 100:11273; Bracken et al., 1994 J. Am. Chem. Soc. 116:6432; Yan et al. 2004 Bioorg. Med. Chem. 14:1403). Alternatively, the peptides are stabilized using the metathesis-based approach, which employed α,α-disubstituted non-natural amino acids containing alkyl tethers (Schafmeister et al., 2000 J. Am. Chem. Soc. 122:5891; Blackwell et al. 1994 Angew. Chem. Int. Ed. 37:3281). Preferably the peptides are stabilized using hydrocarbon stapling. Stapled peptides are chemically braced or "stapled" peptides so that their shape, and therefore their activity, is restored and/or maintained. Stably cross-linking a polypeptide having at least two modified amino acids (a process termed "hydrocarbon stapling") can help to conformationally bestow the native secondary structure of that polypeptide. For example, cross-linking a polypeptide predisposed to have an alpha-helical secondary structure can constrain the polypeptide to its native alpha-helical conformation. The constrained secondary structure can increase resistance of the polypeptide to proteolytic cleavage and also increase hydrophobicity. Stapled BH3 peptides are produced for example, as described in WO05044839A2, herein incorporated by reference in its entirety. Alternatively, the BH3 peptides are cyclic peptides.

Cyclic peptides are prepared by methods known in the art. For example, macrocyclization is often accomplished by forming an amide bond between the peptide N- and C-termini, between a side chain and the N- or C-terminus [e.g., with $K_3Fe(CN)_6$ at pH 8.5] (Samson et al., Endocrinology, 137: 5182-5185 (1996)), or between two amino acid side chains. See, e.g., DeGrado, Adv Protein Chem, 39: 51-124 (1988).

An "isolated" or "purified" protein or biologically active portion thereof is substantially free of cellular material or other contaminating proteins from the cell or tissue source from which the BH3 domain peptide is derived, or substantially free from chemical precursors or other chemicals when chemically synthesized. The language "substantially free of cellular material" includes preparations of BH3 peptides and/or transduction domain peptides in which the protein is separated from cellular components of the cells from which it is isolated or recombinantly produced. In one embodiment, the language "substantially free of cellular material" includes preparations of BH3 domain peptides and/or the transduction domain peptides having less than about 30% (by dry weight) of non-BH3 domain peptide and/or non-transduction domain peptides (also referred to herein as a "contaminating protein"), more preferably less than about 20% of non-BH3 peptide and/or non-transduction domain peptides, still more preferably less than about 10% of non-BH3 peptide and/or non-transduction domain peptides, and most preferably less than about 5% non-BH3 domain peptide and/or non-transduction domain peptides. When the BH3 domain peptide and/or the transduction domain peptides or biologically active portion thereof is recombinantly produced, it is also preferably substantially free of culture medium, i.e., culture medium represents less than about 20%, more preferably less than about 10%, and most preferably less than about 5% of the volume of the protein preparation.

The language "substantially free of chemical precursors or other chemicals" includes preparations of BH3 domain peptides and/or the transduction domain peptides in which the protein is separated from chemical precursors or other chemicals that are involved in the synthesis of the protein. In one embodiment, the language "substantially free of chemical precursors or other chemicals" includes preparations of BH3 domain peptides and/or transduction domain peptides having less than about 30% (by dry weight) of chemical precursors or non-BH3 domain peptide and/or non-transduction domain peptides chemicals, more preferably less than about 20% chemical precursors or non-BH3 domain peptide and/or non-transduction domain peptides chemicals, still more preferably less than about 10% chemical precursors or non-BH3 domain peptide chemicals, and most preferably less than about 5% chemical precursors or non-BH3 domain peptide and/or non-transduction domain peptides chemicals.

The term "biologically equivalent" is intended to mean that the compositions of the present invention are capable of demonstrating some or all of the same apoptosis modulating effects, i.e., release of cytochrome C or BAK oligomerization although not necessarily to the same degree as the BH3 domain polypeptide deduced from sequences identified from cDNA libraries of human, rat or mouse origin or produced from recombinant expression symptoms.

Percent conservation is calculated from the above alignment by adding the percentage of identical residues to the percentage of positions at which the two residues represent a conservative substitution (defined as having a log odds value of greater than or equal to 0.3 in the PAM250 residue weight table). Conservation is referenced to sequences as indicated above for identity comparisons. Conservative amino acid changes satisfying this requirement are: R-K; E-D, Y-F, L-M; V-I, Q-H.

BH3 domain peptides can also include derivatives of BH3 domain peptides which are intended to include hybrid and modified forms of BH3 domain peptides including fusion proteins and BH3 domain peptide fragments and hybrid and modified forms in which certain amino acids have been deleted or replaced and modifications such as where one or more amino acids have been changed to a modified amino acid or unusual amino acid and modifications such as glycosylation so long as the hybrid or modified form retains the biological activity of BH3 domain peptides. By retaining the biological activity, it is meant that cell death is induced by the BH3 polypeptide, although not necessarily at the same level of potency as that of the naturally-occurring BH3 domain polypeptide identified for human or mouse and that can be produced, for example, recombinantly. The terms induced and stimulated are used interchangeably throughout the specification.

Preferred variants are those that have conservative amino acid substitutions made at one or more predicted nonessential amino acid residues. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, a predicted nonessential amino acid residue in a BH3 domain polypeptide is replaced with another amino acid residue from the same side chain family. Alternatively, in another embodiment, mutations can be introduced randomly along all or part of a BH3 coding sequence, such as by saturation mutagenesis, and the resultant mutants can be screened to identify mutants that retain activity.

Also included within the meaning of substantially homologous is any BH3 domain peptide which may be isolated by virtue of cross-reactivity with antibodies to the BH3 domain peptide described herein or whose encoding nucleotide sequences including genomic DNA, mRNA or cDNA may be isolated through hybridization with the complementary sequence of genomic or subgenomic nucleotide sequences or cDNA of the BH3 domain peptides herein or fragments thereof.

Kits

Also included in the invention are kits for performing BH3 Profiling using whole cells. The kit consists of a multi-well plate containing staining components in a mitochondrial buffer and a tube of mitochondrial buffer for the suspension and dispensing of cells into the plate for analysis. Each well of the multi-well plate contains a mixture of JC-1 dye, oligomycin, 2-mercaptoethanol, digitonin, and a peptide or small molecule at twice their final concentration. Optionally, the plate and suspension buffer tube can be frozen for later use along with the suspension buffer tube. To use, the plate and buffer tube are thawed and brought to room temperature. Cells are suspended in buffer, dispensed into the wells of the plate, and analyzed in a fluorescence plate reader using the JC-I red fluorescence at 590 nm with excitation at 545 nm.

The invention will be further illustrated in the following non-limiting examples.

Example 1: Dynamic BH3 Profiling Predicts Sensitivity to Gefitinib and WZ4002

We have found in vitro that dynamic BH3 profiling is effective to predict sensitivity to TKIs gefitinib (Iressa) and the irreversible pyrimidine EGFR kinase inhibitor WZ4002 (that inhibits EGFR even when the T790M mutation is present) in the NSCLC cell lines PC9, parental and with acquired resistance (Zhou et al., Nature 2009).

Three different cell lines were used: PC9, PC9 gefitinib resistant (PC9GR, including the mutation T790M) and PC9GR resistant to WZ4002 (PC9WZR). As a test of our hypothesis, we asked whether cellular toxicity at a late time point of 72 hours could be predicited by a shift in mitochondrial priming at an early time point of 16 hours, a time well before overt cellular toxicity could be observed. We treated the cell lines with the two EGFR kinase inhibitors, gefitinib (1 µM) and WZ4002 (100 nM), for 16 hours and performed the dynamic BH3 profiling analysis. We observed that the BH3 peptide Bim at low concentrations was optimal to observe changes in priming in this model.

Parental PC9 was sensitive to both gefitinib and WZ4002, showing an increase in priming. PC9GR was insensitive to gefitinib, but sensitive to WZ4002, also responding with increased priming. And finally PC9WZR was insensitive to both drugs, although responds to combination of kinase inhibitors (WZ4002 in combination with the MEK inhibitor CI-1040). This increase in priming corresponded very closely to cell death observed at 72 hours (FIG. 1), and was significant (p=0.0052; two-tailed).

Figure 2:
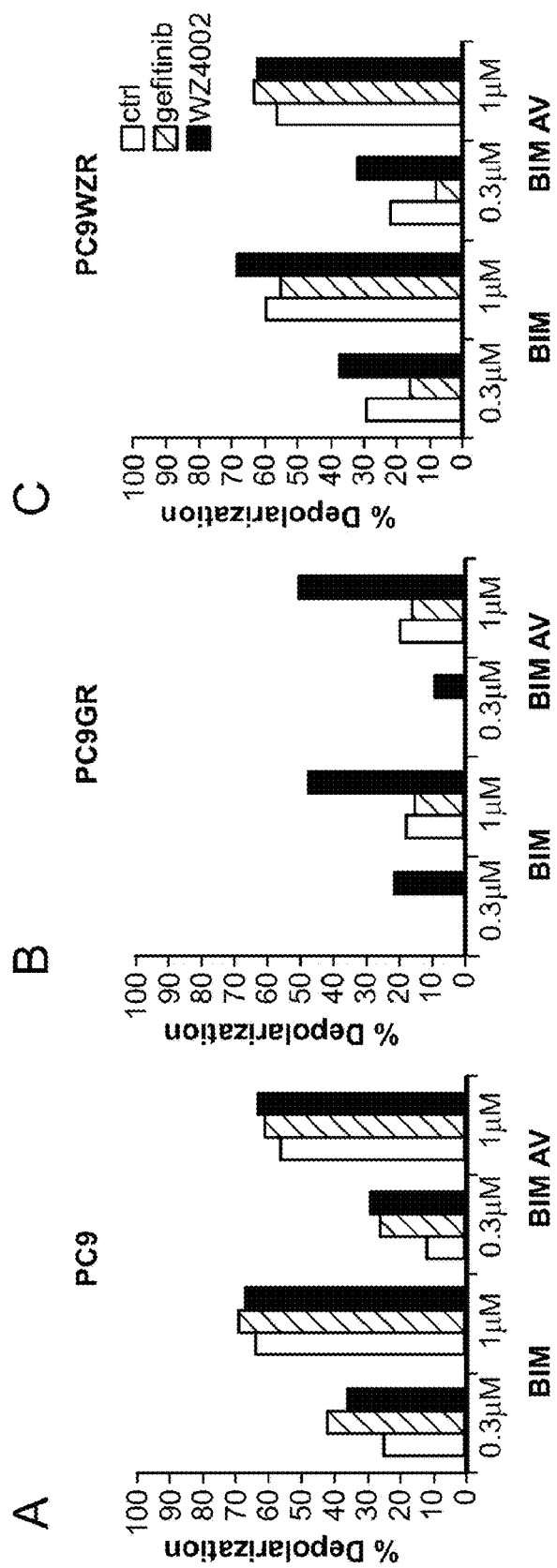
FIG. 2. Mutant BIM AV peptide works like original BIM peptide. Dynamic BH3 profiling in cell lines (A) PC9, (B) PC9GR and (C) PC9WZR exposed to gefitinib 1 µM or WZ4002 100 nM for 16 h, using BIM BH3 peptide Ac-MRPEIWIAQELRRIGDEFNA-NH2 (SEQ ID NO: 1) (0.3 µM or 1 µM) or point-mutated BIM AV BH3 peptide Ac-MRPEIWIAQELRRIGDEFNV-NH2 (SEQ ID NO: 2) (0.3 µM or 1 µM) response to measure priming.

We observed that the BH3 peptide Bim with sequence Ac-MRPEIWIAQELRRIGDEFNA-NH2 (SEQ ID NO:1) at concentrations of 0.3 or 1 µM was optimal in order to predict cell death response to chemotherapy. The point-mutated Bim AV BH3 peptide with sequence Ac-MRPEIWIAQELRRI-GDEFNV-NH2 (SEQ ID NO:2) induced a similar response in these same cell lines (FIG. 2).

Figure 3:
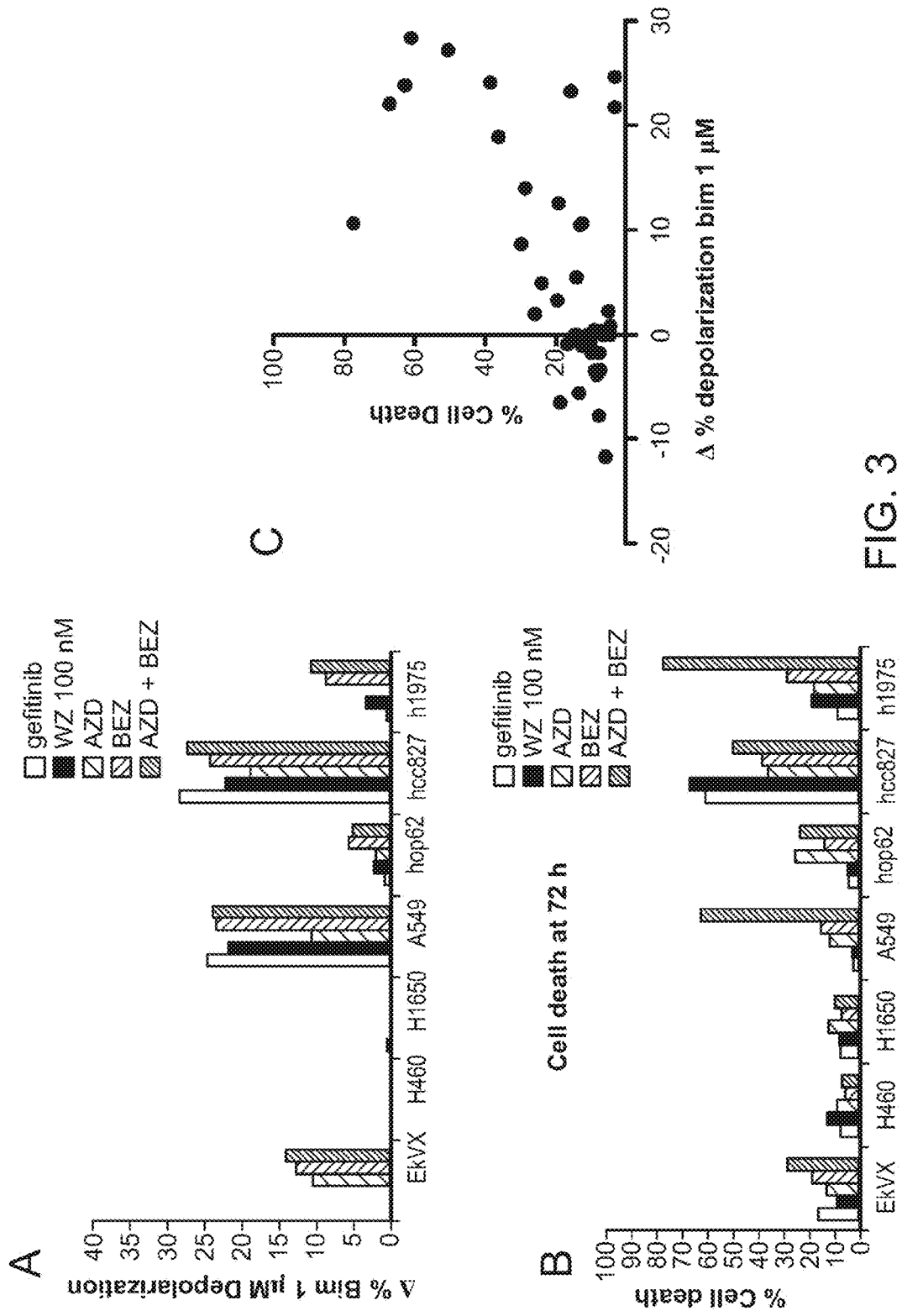
FIG. 3. Dynamic BH3 profiling in NSCLC cell lines. (A) BH3 profiling results on cells exposed to drug for 16 h, using Bim peptide (1 µM) response to measure priming. (B) Cell death was measured at 72 h by FACS using Annexin V/PI staining. (C) Correlation between Δ% depolarization with Bim 1 µM and Cell Death at 72 h, p=0.0014; two-tailed.

We have found a similar significant correlation between dynamic BH3 profiling and cell death using several therapies and several NSCLC lines (FIG. 3). Thus, this technique can be used in vitro to predict chemotherapy response in NSCLC.

Example 2: Dynamic BH3 Profiling Predicts Sensitivity to Imatinib

In order to prove its potential to predict chemotherapy response in different types of cancer, we also tested our hypothesis in cell line models Chronic Myelogenous Leukemia (CML). First we used the murine Ba/F3 cell line, parental and expressing the BCR-ABL fusion protein (p210), present in 95% patients with CML and can be effectively treated with the TKI Gleevec (imatinib). We treated both cells lines with imatinib 1 µM and we performed a dynamic BH3 profiling analysis. (FIGS. 6C and 6D)

Figure 4:
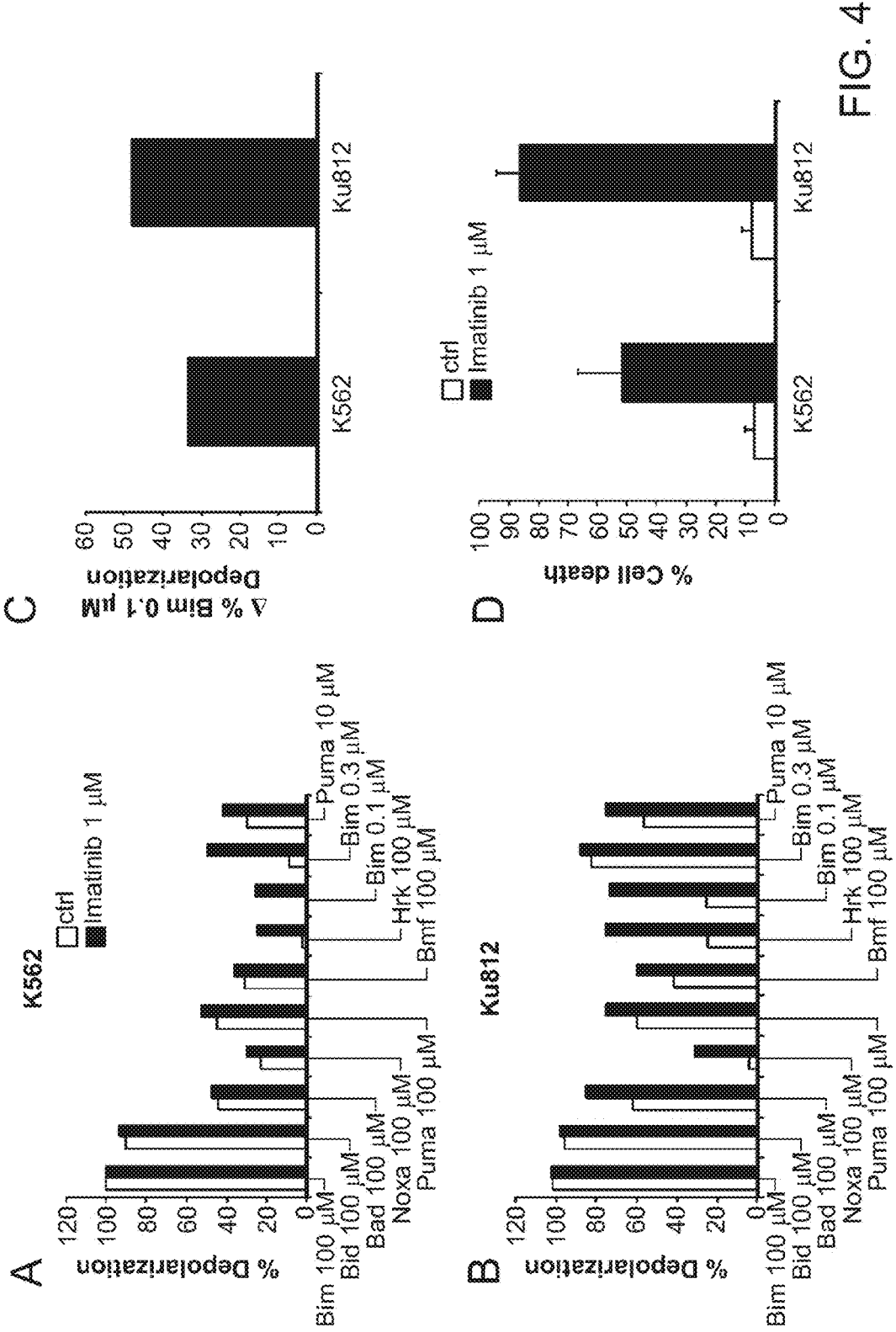
FIG. 4. At left, BH3 profiling results on human CML cell lines (A) K562 and (B) Ku812 treated for 16 h and 8 h with imatinib 1 µM, using several BH3 peptides. At right, correlation between Δ% depolarization with (C) Bim 0.1 µM and (D) cell death at 48 h by FACS using Annexin V/PI staining.

Using this same approach as in Example 1, we analyzed two human CML cell lines, K562 and Ku812, that constitutively express BCR-ABL, exposing them to imatinib and performing the dynamic BH3 profiling analysis. (FIG. 4)

Both K562 and Ku812 cell lines, showed an increase in priming in several peptides used, but as observed previously in NSCLC, a good correlation was observed between the increase in priming using Bim at low concentration (0.1 µM) and cell death at 48 h. Thus, also for CML, dynamic BH3 profiling can be used to predict chemotherapy response.

Figure 5:
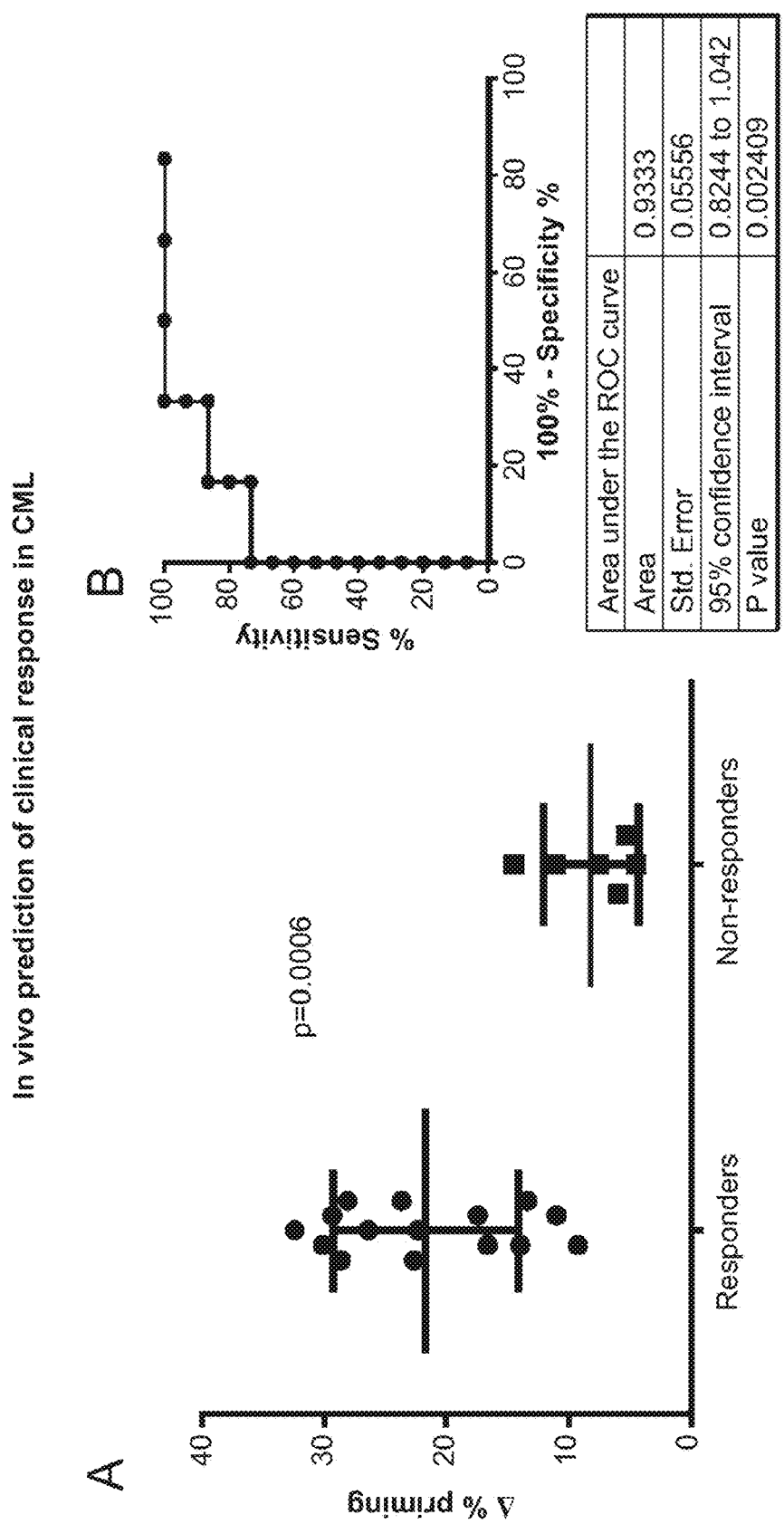
FIG. 5. Dynamic BH3 profiling predicts imatinib response in CML primary samples. DBP predicting capacity in Chronic Myelogenous Leukemia patient samples were tested. (A) Frozen Ficoll purified Bone Marrow primary CML samples were treated for 16 hour with imatinib 1 and 5 µM, and DBP was then performed. Results are expressed as Δ% priming. Those samples obtained from patients that responded to imatinib treatment in clinic, showed a significantly higher Δ% priming in our DBP analysis, as opposed to those samples obtained from patients that relapsed. (B) A Receiver Operating Characteristic curve analysis for this set of samples was performed. The area under the ROC curve is 0.94, indicating the DBP could be used as binary predictor for CML patients to predict if they will benefit from imatinib treatment.

An important part of the application of this invention is the prediction of response to therapy in vivo. In FIG. 5, we show that pretreatment analysis of three patient chronic myelogenous leukemia sample correctly identifies the two that will respond and the one that will not respond to imatinib using dynamic BH3 profiling.

Figure 6:
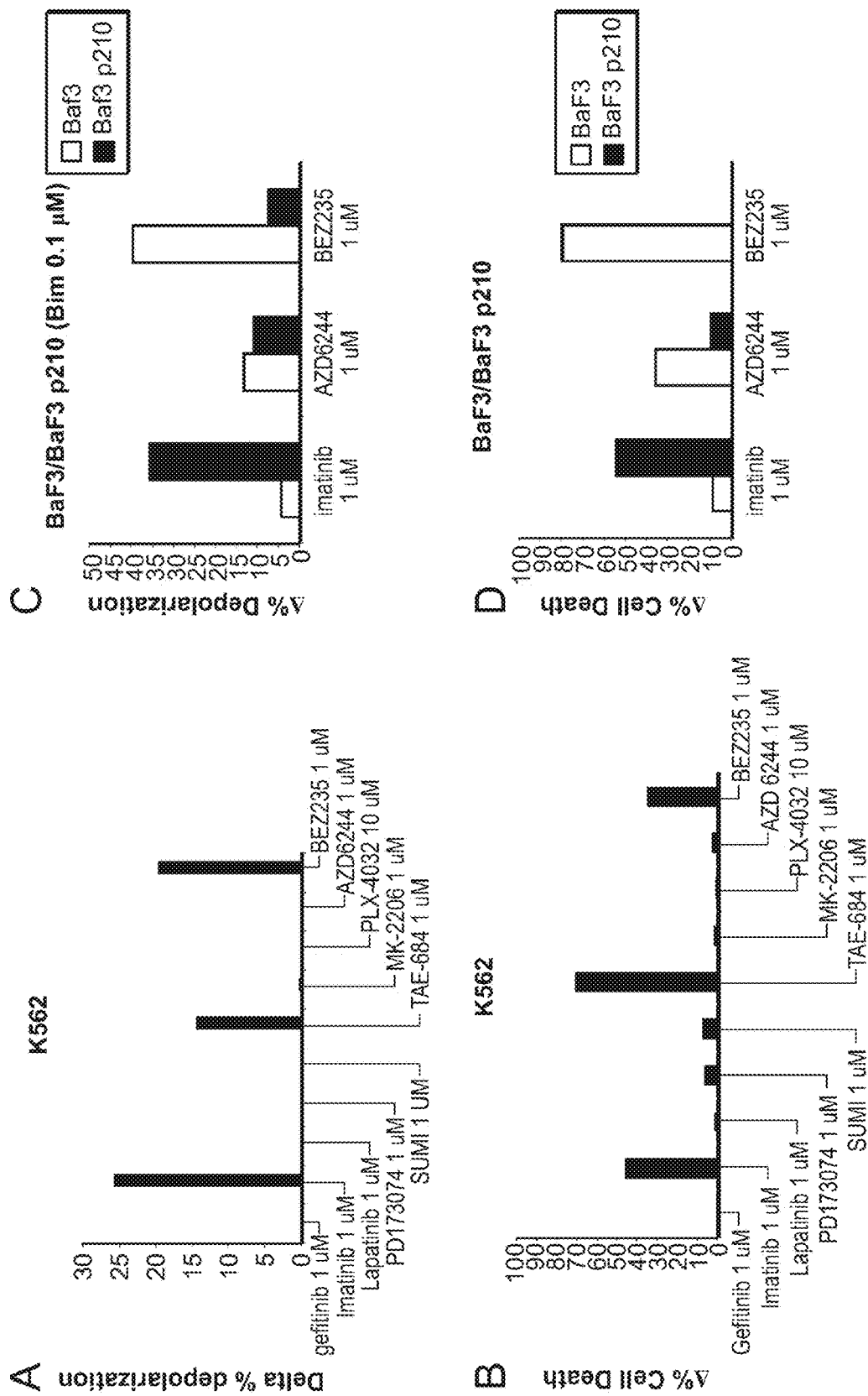
FIG. 6. Dynamic BH3 profiling accurately predicts leukemia cell death response to targeted therapies. (A) K562 myeloid leukemia cells were exposed to a panel of inhibitors of a range of kinases for 16 hours, and dynamic BH3 profiling was performed. The change in depolarization caused by the BIM BH3 peptide following drug treatment is shown. Note that significant changes were found only for imatinib (BCR-Abl inhibitor), TAE-684 (ALK), and BEZ235 (PI3K/mTOR). (B) K562 cells were exposed to the same panel of drugs for 72 hours and the cell death response was evaluated by Annexin V/PI. Note that dynamic BH3 profiling accurately predicted the expected killing by imatinib, but also the unexpected killing by TAE-684 and BEZ235. (C) Dynamic BH3 profiling of BaF3 murine leukemia cells with and without p210 reveals differential priming changes induced by different drugs after 16 hour exposure. (D) Cytotoxicity (Annexin V/PI) after 48 hours exposure confirms prediction of Dynamic BH3 profiling. (E) Dynamic BH3 profiling of Ku812 AML cells exposed to epigenetic modifying agents (from Project 4). Imatinib is a positive control. BET inhibitor JQ1, but not compounds A (DOT1L inhibitor) and B (EZH2 inhibitor), increases priming and is predicted to cause cell death. (F) Imatinib and JQ1, but not compounds A and B, induce cell death as predicted by dynamic BH3 profiling.
Figure 6:
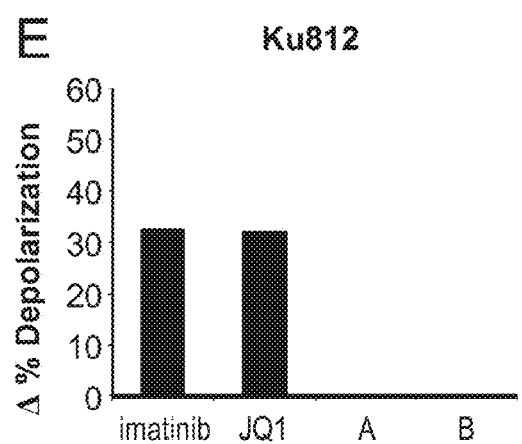
Figure 6:
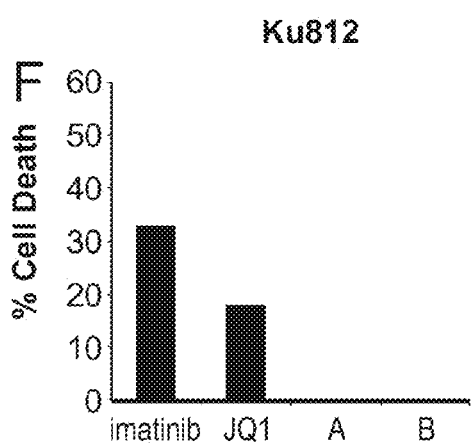

Example 3: Dynamic BH3 Profiling Predicts Sensitivity to Multiple Agents in Leukemia Cells Using a variety of leukemia cells as a model, we tested the ability of dynamic BH3 profiling to identify agents that selectively cause cell death (FIG. 6). We found that dynamic BH3 profiling correctly identified drugs that would cause cell death across multiple drugs and cell lines.

Example 4: BH3 Profiling Predicts Clinical Response to Imatinib in Patients with Chronic Myelogenous Leukemia An essential demonstration of the utility of Dynamic BH3 Profiling is that it predicts clinical response in testing of actual primary patient cancer cells. In FIG. 5, we performed Dynamic BH3 Profiling on 24 samples obtained from patients with CML. In FIG. 5A, we compare our Dynamic BH3 Profiling results with clinical response. In FIG. 5B, we use a receiver operating characteristic curve to demonstrate that Dynamic BH3 Profiling predicts response to imatinib in CML patients with high sensitivity and specificity.

Figure 7:
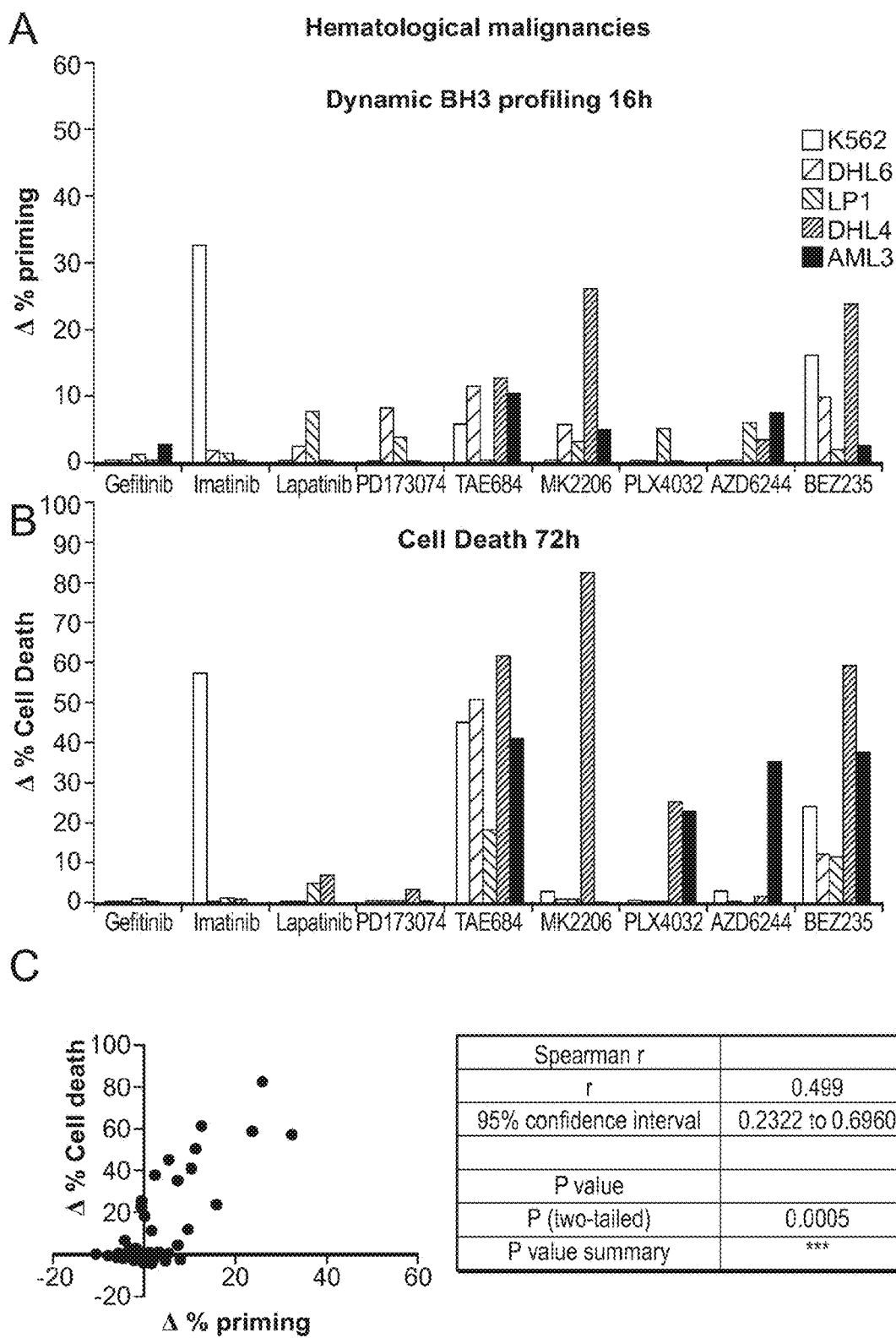
FIG. 7. Identifying the optimal treatment in hematological malignancies using DBP. Several drugs targeting either key membrane receptors: geftinib (EGFR inh), imatinib (Abl inh.), lapatinib (HER2 inh.), PD173074 (FGFR inh.) and TAE-684 (Alk inh.); or important intracellular kinases: MK-2206 (Akt inh.), PLX-4032 (Braf$^{V600E}$ inh.), AZD-6244 (MEK inh.) and BEZ-235 (PI3K/mTOR inh.) were selected, and they were tested in several human hematological cancer cell lines: K562 (Chronic Myelogenous leukemia), DHL6 (Diffuse large B-cell lymphoma), LP1 (Multiple Myeloma), DHL4 (Diffuse large B-cell lymphoma) and AML3 (Acute Myeloid Leukemia). (A) DBP (16 hour incubation) results expressed as $\Delta\%$ priming and (B) cell death measurements at 72 hours using Annexin V/PI staining expressed as $\Delta\%$ Cell Death, (C) showed as significant correlation. Therefore, DBP can predict the optimal treatment for hematological malignancies' cell lines.
Figure 8:
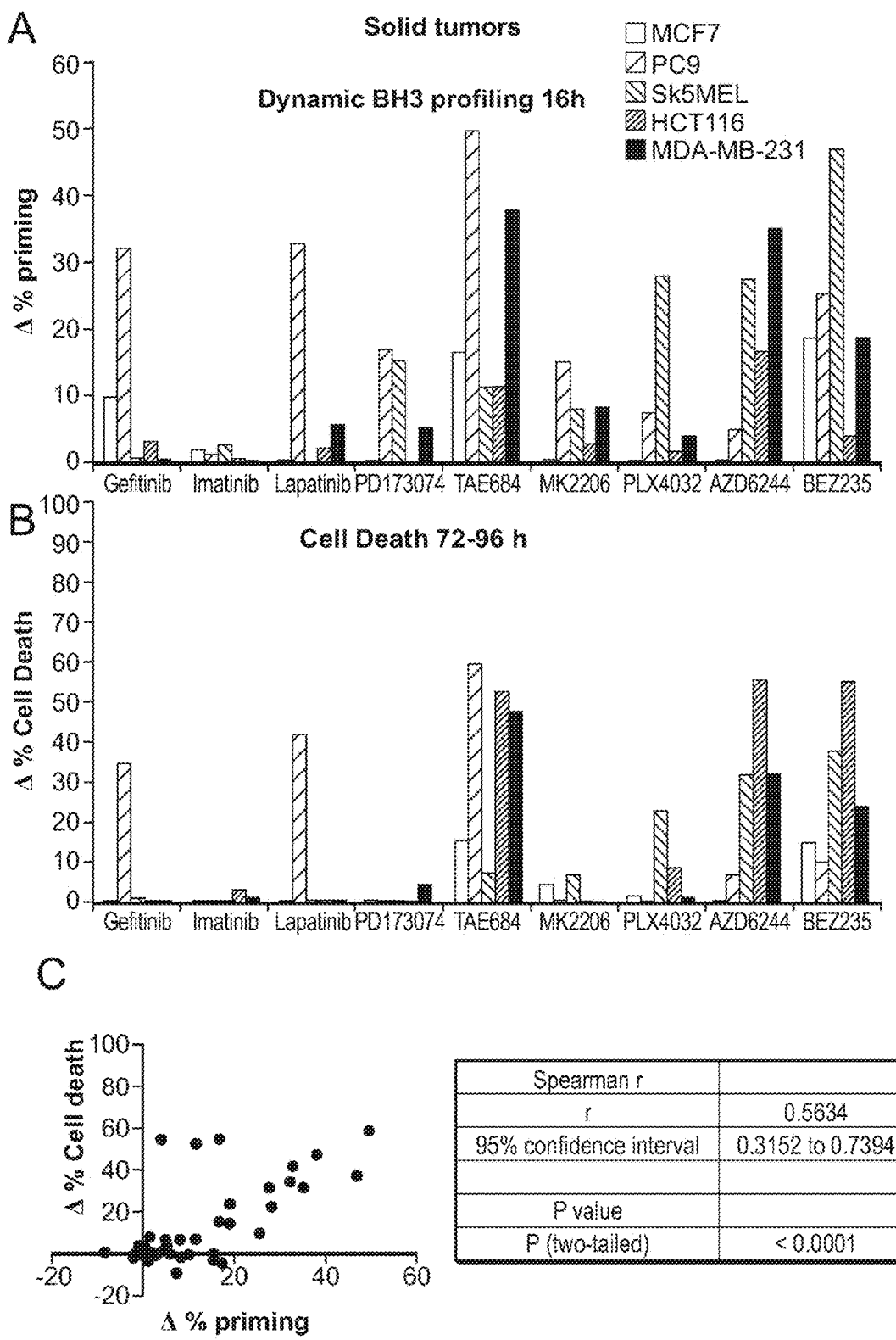
FIG. 8. Identifying the optimal treatment in solid tumors using DBP. The same panel of kinase inhibitors used in FIG. 7 was tested on several human solid tumor cell lines: MCF7 (Breast Cancer), PC9 (Non-Small Cell Lung Cancer), Sk5mel (Melanoma), HCT116 (Colon carcinoma) and MDA-MB-231 (Breast Cancer). (A) DBP (16 hour incubation) results expressed as $\Delta\%$ priming and (B) cell death measurements at 72-96 hours using Annexin V/PI staining expressed as $\Delta\%$ Cell Death, (C) showed a significant correlation. Therefore, DBP can also predict the optimal treatment for solid tumors' cell lines.
Figure 9:
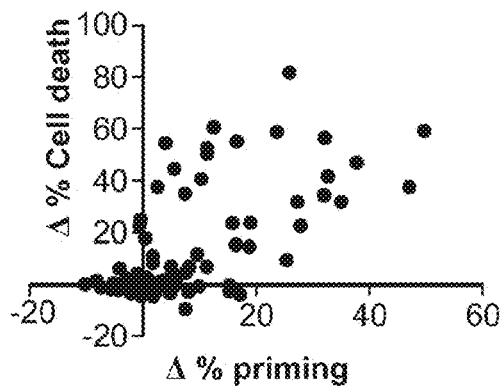
FIG. 9. Dynamic BH3 profiling is a good binary predictor. (A) Compilation of FIG. 7 and FIG. 8 results, showing a significant correlation between $\Delta\%$ priming and $\Delta\%$ Cell Death for all the cell lines. (B) A Receiver Operating Characteristic curve analysis was performed. The area under the ROC curve is 0.87, indicating that is a good binary predictor for chemotherapy response in cell lines.
Figure 9:
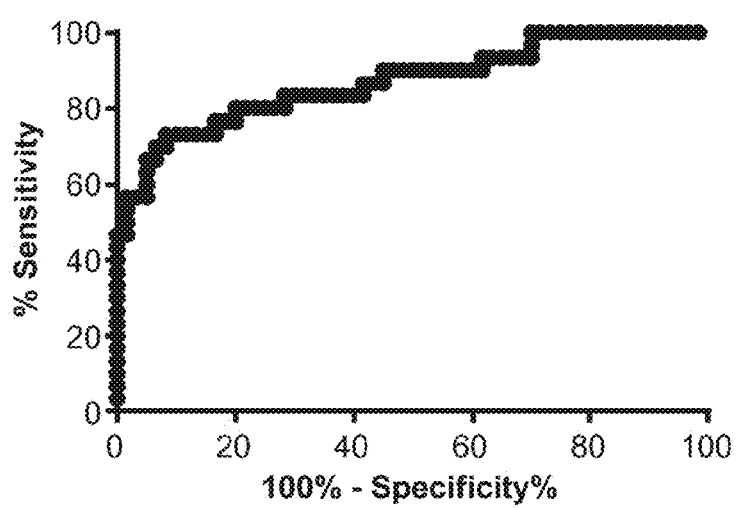
Figure 10:
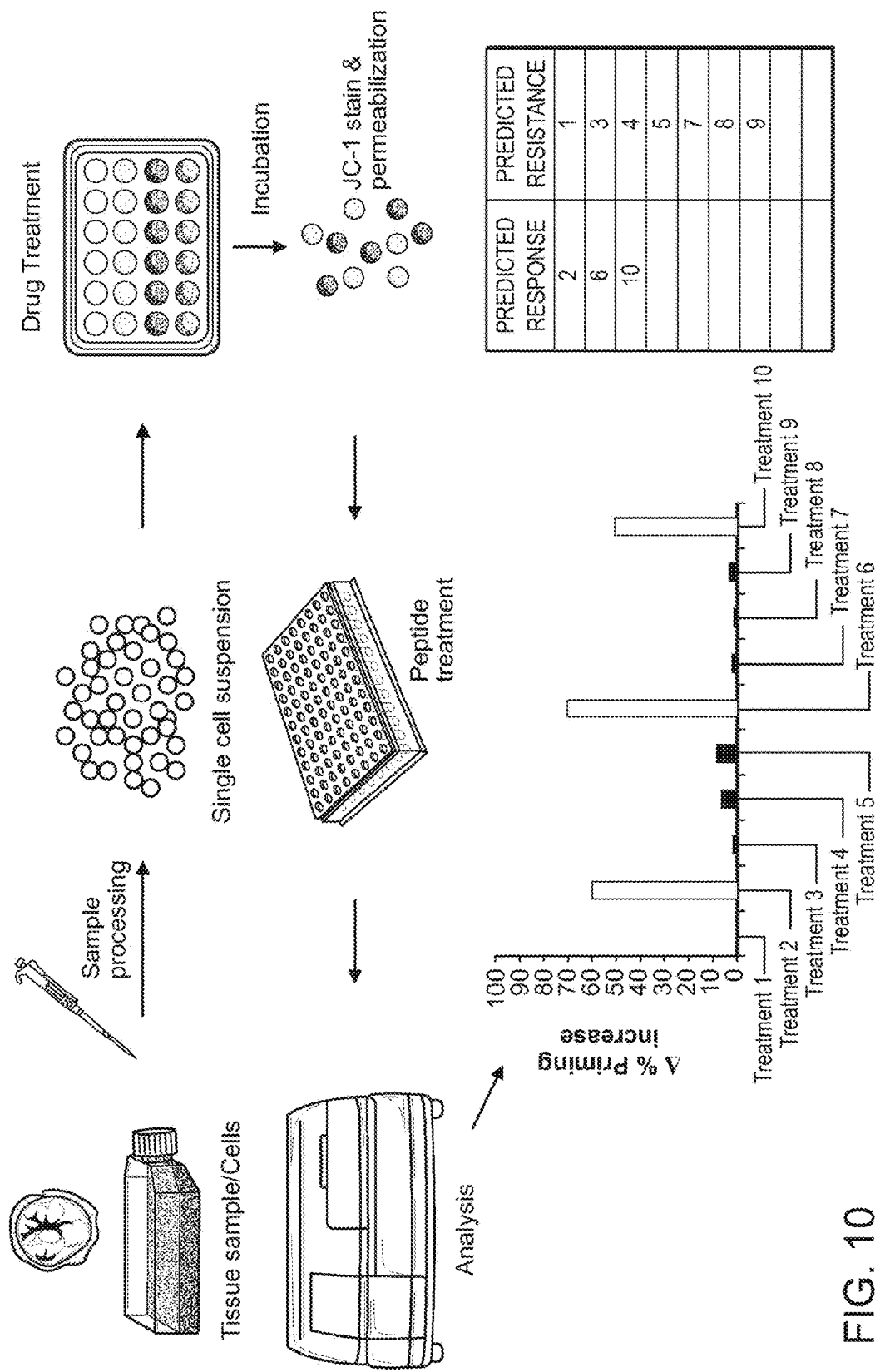
FIG. 10 is a schematic illustrating the methods of the invention.

Example 5: BH3 Profiling Predicts Sensitivity to Multiple Agents Across Multiple Cancer Cell Lines In FIG. 7, we use 9 agents to perform Dynamic BH3 Profiling on 5 cell lines derived from hematologic malignancies using a 16 hour drug exposure. The Dynamic BH3 Profiling at 16 hours (7A) predicted cytotoxicity at 72 hours 7(B) with great statistical significance (7C). In FIG. 8, we use 9 agents to perform Dynamic BH3 Profiling on 5 cell lines derived from solid tumors using a 16 hour drug exposure. The Dynamic BH3 Profiling at 16 hours (8A) predicted cytotoxicity at 72 hours (8B) with great statistical significance (8C).

Figure 11A:
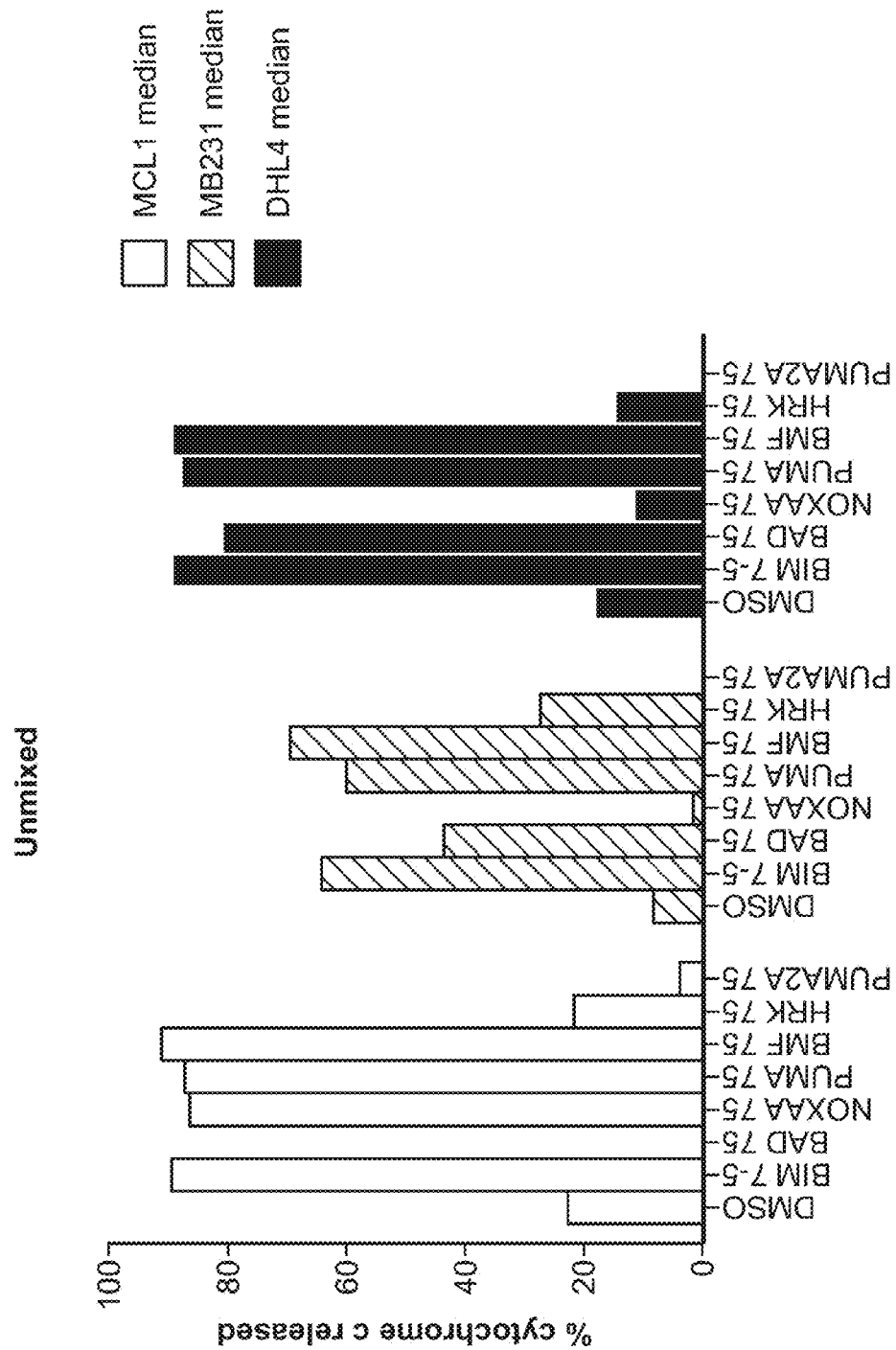
FIG. 11 is a series of bar graphs demonstrating that iBH3 can reproduce the profile of individual subpopulations with mixed populations. Samples profiled individually (unmixed as shown in FIG. 11A) or as a complex mixture (mixed as shown in FIG. 11B) produce the same profile.
Figure 11B:
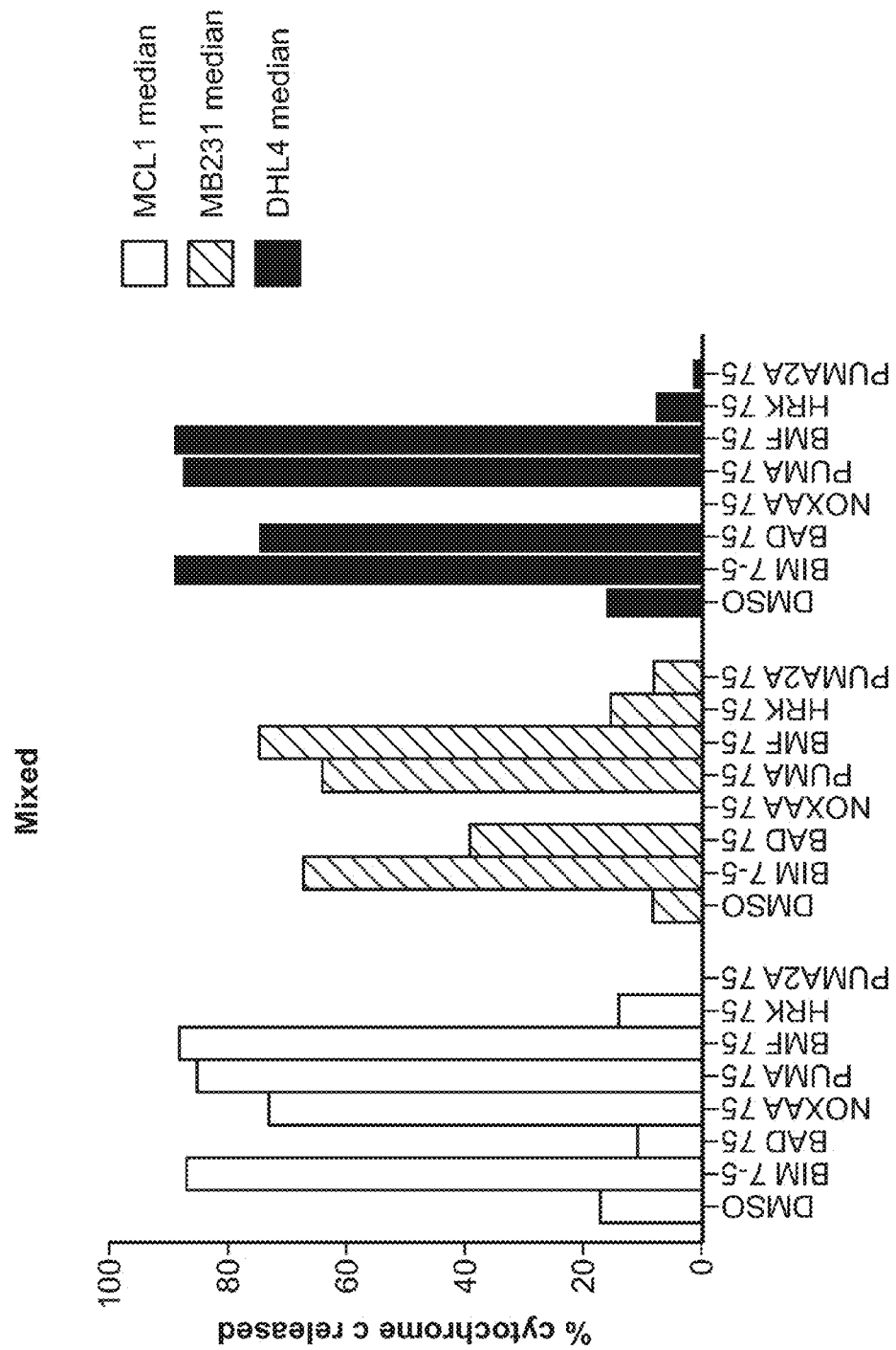
Figure 12A:
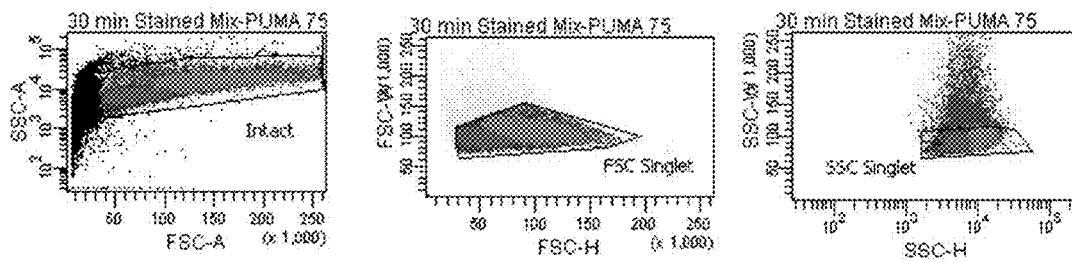
FIG. 12 is a series of panels showing how iBH3 defines cell populations and measures cellular response to profiling. Representative FACS data (FIG. 12A and FIG. 12B) demonstrates the isolation of subpopulations within the mixed sample in FIG. 11.
Figure 12B:
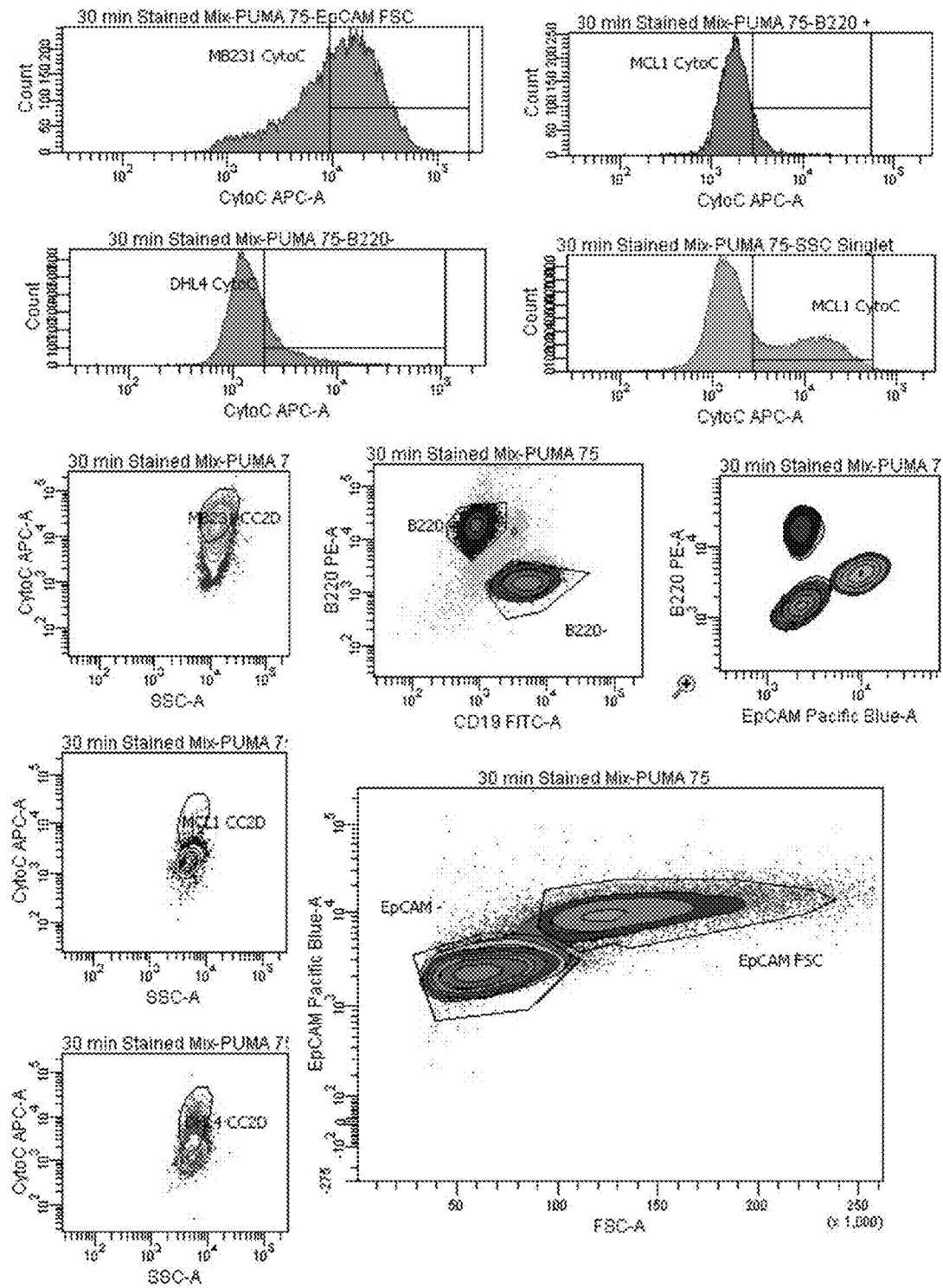
Figure 13:
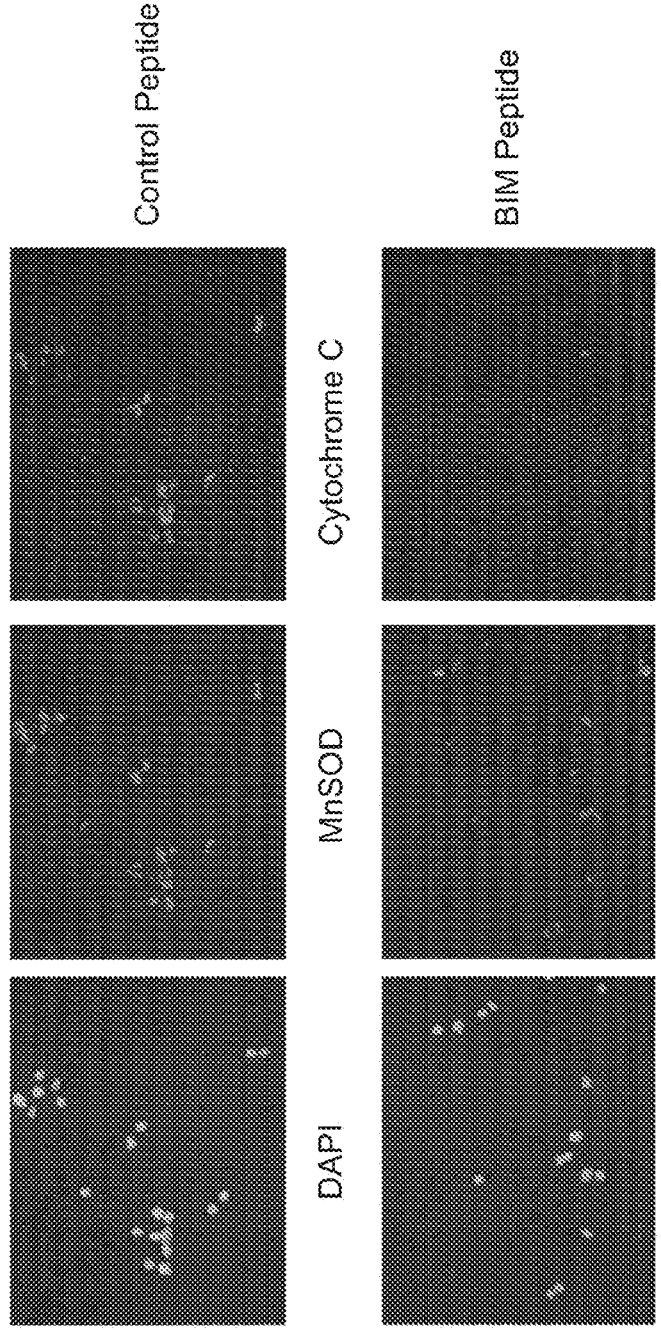
FIG. 13 is a series of fluorescent microscopy images that show the loss of cytochrome c in response to peptide treatment measured by microscopy. Cells are located by DAPI staining of their nuclei, mitochondria are located by staining of a mitochondrial marker (MnSOD) adjacent to nuclei, and cytochrome c staining is correlated with regions of mitochondrial marker staining. An inert control peptide shows cytochrome c staining in regions of MnSOD staining while BIM peptide causes almost total loss of cytochrome c from all regions of MnSOD staining.
Figure 14A:
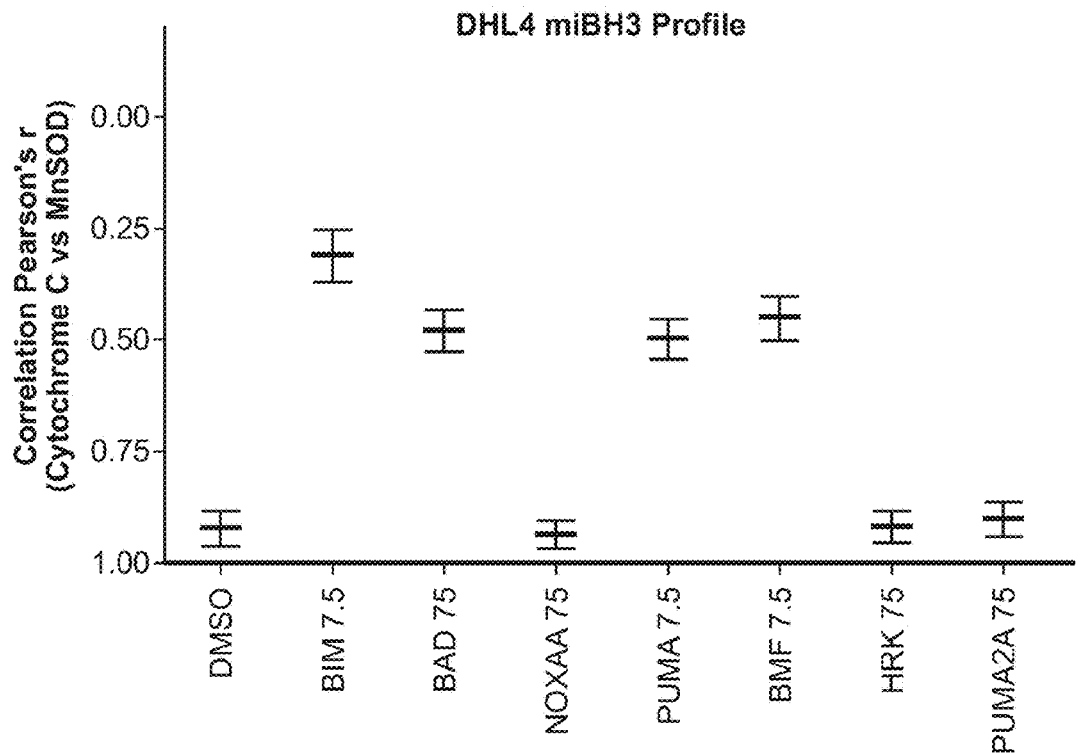
FIG. 14 is a series of bar graphs showing correlation of miBH3 profiles with known profiles. The miBH3 profile of the SuDHL4 cell line (FIG. 14A) shows loss of correlation between cytochrome c and MnSOD channels in response to BH3 peptides. Release of cytochrome c and loss of correlation for BIM, BAD, PUMA, and BMF peptides match the loss of cytochrome c measured by other BH3 profiling methods shown in FIG. 14B.
Figure 14B:
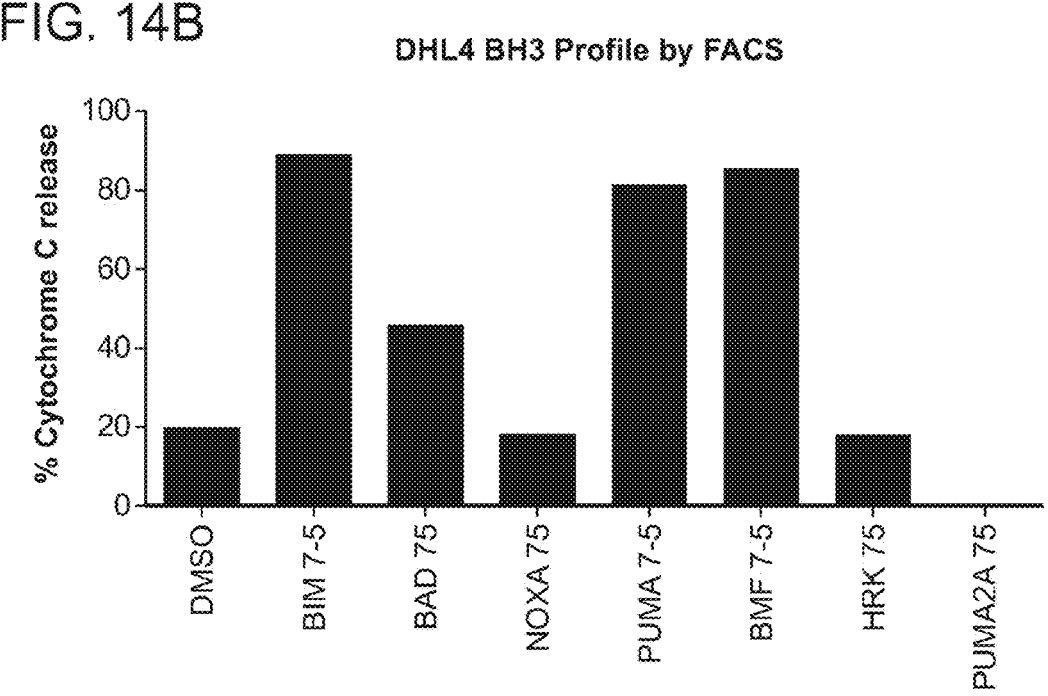

Example 6: IBH3: BH3 Profiling by Direct Measurement of Retained Cytochrome C by FACS iBH3 adds a key fixation step to prior protocols for BH3 profiling. This produced a better signal, increased sample stability, and improved staining to discriminate subsets in complex clinical samples. Primary tissue or cell cultures are dissociated into single cell suspensions, optionally stained for cell surface markers, and suspended in DTEB Mitochondrial buffer (BH3 profiling in whole cells by fluorimeter or FACS. Methods. 2013 Apr. 20. Epub ahead of print). The suspended cells are then added to wells containing DTEB supplemented with digitonin (a permeabilizing agent) and either peptides or small molecules, which can be prepared and frozen in sample tubes or plates, to allow the molecules or peptides to access the mitochondria and allow for the free diffusion of cytochrome c out of permeabilized mitochondria and out of the cell. Cells are exposed to peptides/small molecules for period of time before a short aldehyde fixation followed by neutralization with a Tris/Glycine buffer. Anti-cytochrome c antibody is then added to each well as a concentrate with saponin, fetal bovine serum, and bovine serum albumin to stain cytochrome c retained by the cells. Other antibodies to intracellular targets can be added at this time. Cells are analyzed by FACS to provide single cell measurements of cytochrome c after perturbation with peptides or small molecules to provide diagnostic response signatures. In FIG. 11, iBH3 faithfully reproduces the profile of individual subpopulations within mixed populations. Samples profiled individually (unmixed) or as a complex mixture (mixed) produce the same profile. This ability to discriminate subpopulations can be applied to any antigen or signal whether intra- or extracellular.

This is an improvement over ELISA based BH3 profiling because it can analyze sub-populations within samples, and it is the only method capable of profiling using both extracellular and intracellular markers. Furthermore, it is capable of performing this analysis in high throughput format and can be used with pre-made frozen test plates without the time sensitivity of live mitochondrial potential measurements using potentiometric dyes.

Example 5: MicroBH3: Single Cell BH3 Profiling by Immunofluorescence Microscopy

MicroBH3 (miBH3) is a BH3 profiling method where the measurement of the mitochondrial effect of BH3 peptides have on individual cells by microscopy. To accomplish this, cells are immobilized on polyamine or poly-lysine coated surfaces and treated with low concentrations of digitonin in a mitochondrial buffer to permeabilize the plasma membrane and grant access to the mitochondria without cell disruption. Fixed concentrations of BH3 peptides or chemical compounds are added for a fixed time, generally 45-90 min, before formaldehyde fixation and permeabilization by methanol and/or triton x-100 for intracellular staining of cytochrome C and a mitochondrial marker such as MnSOD. Stained cells are counterstained with nuclear stains such as DAPI, and fluorescent images are acquired in nuclear, mitochondrial, and cytochrome c channels. Automated analysis is performed using software such as Celiprofiler to locate nuclei, define regions adjacent to nuclei that have mitochondria, and then correlate the presence of cytochrome c with the location of the mitochondria. Loss of localization indicates a loss of cytochrome c and a reaction to the peptide or compound. This method allows the response of cells to BH3 peptides or compounds and determine their apoptotic propensity, or priming, at a single cell level. Previous methods of analyzing mitochondrial integrity using potential sensitive fluorescent dyes use intact, not permeabilized, cells and cannot be used with BH3 peptides as they are not cell permeant. Permeabilized cells treated with potential sensitive change shape and are difficult to keep in focus for the necessary time courses and are sensitive to timing. Fixed cells by this method can be readily stopped at the fixation step and can be analyzed weeks after acquisition as well as readily re-analyzed if needed.

Other Embodiments

While the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method of predicting sensitivity of a cancer cell population to a cytotoxic agent comprising:
   a) permeabilizing a test cell portion from a cancer cell population, wherein the test cell portion has been contacted with a panel of test cytotoxic agents;
   b) contacting mitochondria of the test cell portion with a pro-apoptotic BH3 domain peptide, wherein the test cell portion has been permeabilized to permit the BH3 domain peptide access to said mitochondria;
   c) measuring the amount of BH3 domain peptide-induced mitochondrial outer membrane permeabilization in mitochondria of permeabilized cells in the test cell portion after contacting with the BH3 domain peptide; and
   d) comparing the amount of BH3 domain peptide-induced mitochondrial outer membrane permeabilization in mitochondria of a permeabilized test cell within the test cell portion to the amount of BH3 domain peptide-induced mitochondrial outer membrane permeabilization in mitochondria of a control cell portion from the cancer cell population, wherein the control cell portion has not been contacted with the panel of test cytotoxic agents,
   wherein an increase in the amount of mitochondrial outer membrane permeabilization in mitochondria of the permeabilized test cell within the test cell portion compared to the amount of mitochondrial outer membrane permeabilization in mitochondria of the control cell portion indicates that the cancer cell population is sensitive to a cytotoxic agent of the panel of test cytotoxic agents.

2. The method of claim 1, wherein said mitochondrial outer membrane permeabilization is determined by measuring i) loss of mitochondrial membrane potential from mitochondria of the test cell portion, or ii) release of mitochondrial inter-membrane space molecules from mitochondria of the test cell portion.

3. The method of claim 2, further comprising measuring the loss of mitochondrial membrane potential from mitochondria of the test cell portion by contacting said test cell portion with a potentiometric dye and measuring emission of said potentiometric dye.

4. The method of claim 3, wherein said potentiometric dye is 5,5',6,6'-tetrachloro-1,1'3,3'-tetraethylbenzimidazolylcarbocyanine iodide (JC-1) or dihydrorhodamine 123.

5. The method of claim 2, further comprising measuring the release of mitochondrial inter-membrane space molecules from mitochondria of the test cell portion by contacting said mitochondria of the test cell portion with an antibody for cytochrome C, SMAC/Diablo, Omi, adenylate kinase-2 or apoptosis-inducing factor.

6. The method of claim 1, further comprising contacting said test cell portion with an antibody for an intracellular or extracellular marker to permit discrimination between cell subpopulations in the test cell portion based on expression of the intracellular or extracellular marker.

7. The method of claim 1, further comprising fixing the test cell portion prior to measuring mitochondrial outer membrane permeabilization in mitochondria of the test cell portion.

8. The method of claim 7, wherein the test cell portion is fixed on a solid surface.

9. The method of claim 1, wherein said BH3 domain peptide is derived from the BH3 domain of a BH3 interacting domain death agonist (BID), a Bcl-2 interacting mediator of cell death (BIM), a Bcl-2-associated death promoter (BAD), a Noxa, a p53 up-regulated modulator of apoptosis (PUMA), a Bcl-2-modifying factor (BMF), or a harakiri (HRK) polypeptide.

10. The method of claim 1, wherein said BH3 domain peptide is selected from the group consisting of SEQ ID NO: 1, 2, 3, 4, 5, 6, 7, 8, 9, 10, 11, 12, 13, and 14.

11. The method of claim 1, wherein said panel of test cytotoxic agents include a chemotherapeutic agent.

12. The method of claim 11, wherein the chemotherapeutic agent is a targeted chemotherapeutic agent.

13. The method claim 11, wherein the chemotherapeutic agent is a kinase inhibitor.

14. The method of claim 1, wherein a decrease or no change in the amount of mitochondrial outer membrane permeabilization in mitochondria of the permeabilized test cell within the test cell portion compared to the amount of mitochondrial outer membrane permeabilization in mitochondria of the control cell portion indicates that the cancer cell population is resistant to the panel of test cytotoxic agents.

* * * * *

UNITED STATES PATENT AND TRADEMARK OFFICE
CERTIFICATE OF CORRECTION

PATENT NO. : 10,393,733 B2
APPLICATION NO. : 14/429272
DATED : August 27, 2019
INVENTOR(S) : Anthony Letai et al.

It is certified that error appears in the above-identified patent and that said Letters Patent is hereby corrected as shown below:

In the Claims

In Column 24, Claim 2, Line 55, the text:
"chondria of the test cell portion, or ii) release of mitochon-"
Should be replaced with the text:
--chondria of permeabilized cells in the test cell portion, or ii) release of mitochon--.

In Column 24, Claim 3, Line 60, the text:
"chondria of the test cell portion by contacting said test cell"
Should be replaced with the text:
--chondria of permeabilized cells in the test cell portion by contacting said test cell--.

In Column 25, Claim 5, Lines 1-2, the text:
"ecules from mitochondria of the test cell portion by contacting said mitochondria of the test cell portion with an"
Should be replaced with the text:
--ecules from mitochondria of permeabilized cells in the test cell portion by contacting said mitochondria of permeabilized cells in the test cell portion with an--.

In Column 25, Claim 7, Line 13, the text:
"membrane permeabilization in mitochondria of the test cell"
Should be replaced with the text:
--membrane permeabilization in mitochondria of permeabilized cells in the test cell--.

Signed and Sealed this
Twenty-sixth Day of November, 2019

Andrei Iancu
*Director of the United States Patent and Trademark Office*